US009974461B2

United States Patent
Shin et al.

(10) Patent No.: US 9,974,461 B2
(45) Date of Patent: May 22, 2018

(54) ELECTROCARDIOGRAM (ECG) SENSOR CHIP, SYSTEM ON CHIP (SOC), AND WEARABLE APPLIANCE

(71) Applicants: Seung Chul Shin, Seoul (KR); Hyung Jong Ko, Seongnam-si (KR); Jung Su Kim, Yongin-si (KR); Yong In Park, Seoul (KR); Won Hyuk Jung, Yongin-si (KR); Yun Cheol Han, Yongin-si (KR)

(72) Inventors: Seung Chul Shin, Seoul (KR); Hyung Jong Ko, Seongnam-si (KR); Jung Su Kim, Yongin-si (KR); Yong In Park, Seoul (KR); Won Hyuk Jung, Yongin-si (KR); Yun Cheol Han, Yongin-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days. days.

(21) Appl. No.: 14/840,154

(22) Filed: Aug. 31, 2015

(65) Prior Publication Data

US 2017/0055869 A1    Mar. 2, 2017

(30) Foreign Application Priority Data

Nov. 17, 2014    (KR) .................. 10-2014-0160011

(51) Int. Cl.
*A61B 5/0428*    (2006.01)
*A61B 5/00*    (2006.01)
(Continued)

(52) U.S. Cl.
CPC ........ *A61B 5/04288* (2013.01); *A61B 5/0404* (2013.01); *A61B 5/0456* (2013.01);
(Continued)

(58) Field of Classification Search
CPC ... A61B 5/0402; A61B 5/0404; A61B 5/0428; A61B 5/04288; A61B 5/0432; A61B 5/04325
See application file for complete search history.

(56) References Cited

U.S. PATENT DOCUMENTS 7,974,689 B2    7/2011    Volpe et al.
8,600,486 B2    12/2013    Kaib et al.
(Continued)

FOREIGN PATENT DOCUMENTS

JP    05-293091    11/1993
JP    2004-0321252    11/2004
(Continued)

OTHER PUBLICATIONS

Wilson, Frank et al. "The Potential Variations Produced by the Heart Beat at the Apices of Einthoven's Triangle". American Heart Journal, vol. 7, iss. 2, Dec. 1931, pp. 207-211.*
(Continued)

*Primary Examiner* — Allen Porter, Jr.
(74) *Attorney, Agent, or Firm* — Volentine, Whitt & Francos, PLLC

(57) ABSTRACT

An ECG sensor chip used in a wearable appliance includes; a switch controlled by a switching signal, an amplifier that amplifies a difference between first and second ECG signals, and a location indicator that generates the switching signal. The switch passes either a first ECG signal or second ECG signal in response to the switching signal.

25 Claims, 27 Drawing Sheets

(51) Int. Cl.
*A61B 5/0404* (2006.01)
*A61B 5/0432* (2006.01)
*A61B 5/0456* (2006.01)

(52) U.S. Cl.
CPC .......... *A61B 5/04325* (2013.01); *A61B 5/681* (2013.01); *A61B 5/6803* (2013.01); *A61B 5/6824* (2013.01); *A61B 5/6833* (2013.01); *A61B 5/7225* (2013.01); *A61B 5/746* (2013.01)

(56) References Cited

U.S. PATENT DOCUMENTS

| | | | |
|---|---|---|---|
| 2009/0007661 A1* | 1/2009 | Nasiri | G01P 1/023 |
| | | | 73/504.03 |
| 2010/0076331 A1* | 3/2010 | Chan | A61B 5/0006 |
| | | | 600/522 |
| 2012/0035435 A1 | 2/2012 | Choi et al. | |
| 2012/0289809 A1* | 11/2012 | Kaib | A61B 5/04085 |
| | | | 600/388 |
| 2014/0206948 A1 | 7/2014 | Romem | |
| 2014/0221849 A1 | 8/2014 | Farringdon et al. | |
| 2015/0087948 A1* | 3/2015 | Bishay | A61B 5/04087 |
| | | | 600/382 |
| 2015/0190069 A1* | 7/2015 | Tao | A61B 5/04012 |
| | | | 600/509 |
| 2015/0335283 A1* | 11/2015 | Fish | A61B 5/02416 |
| | | | 600/324 |
| 2016/0262695 A1* | 9/2016 | Zhang | A61B 5/022 |

FOREIGN PATENT DOCUMENTS

| | | | |
|---|---|---|---|
| KR | 20060091187 A | | 8/2006 |
| KR | 1038432 | | 6/2011 |
| KR | 101219151 B1 | | 1/2013 |
| WO | WO 2015/030712 | * | 5/2015 |

OTHER PUBLICATIONS

Einthoven, W. et al. "On the Direction and Manifest Size of the Variations of Potential in the Human Heart and on the Influence of the Position of the Heart on the Form of the Electrocardiogram". American Heart Journal, vol. 40, iss 2, Aug. 1950, pp. 163-211.*

* cited by examiner

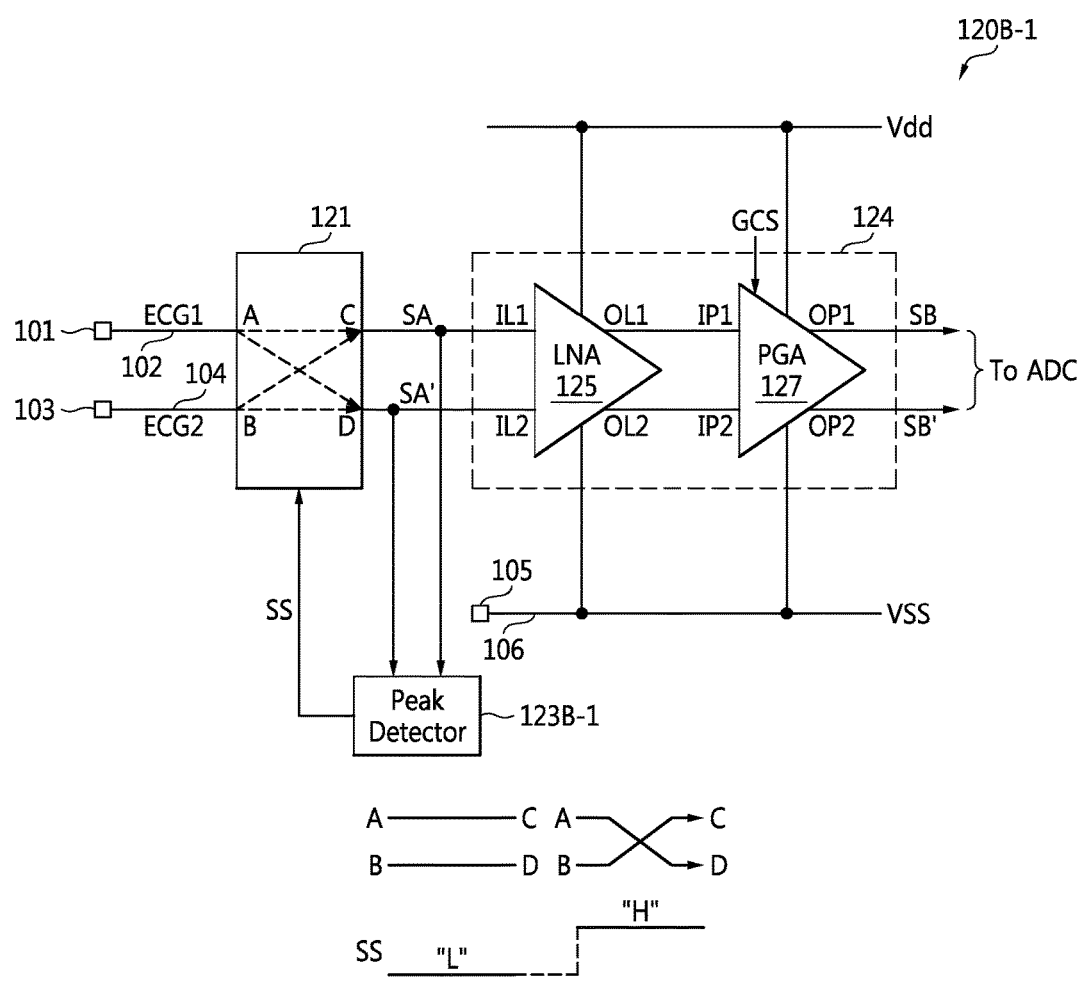

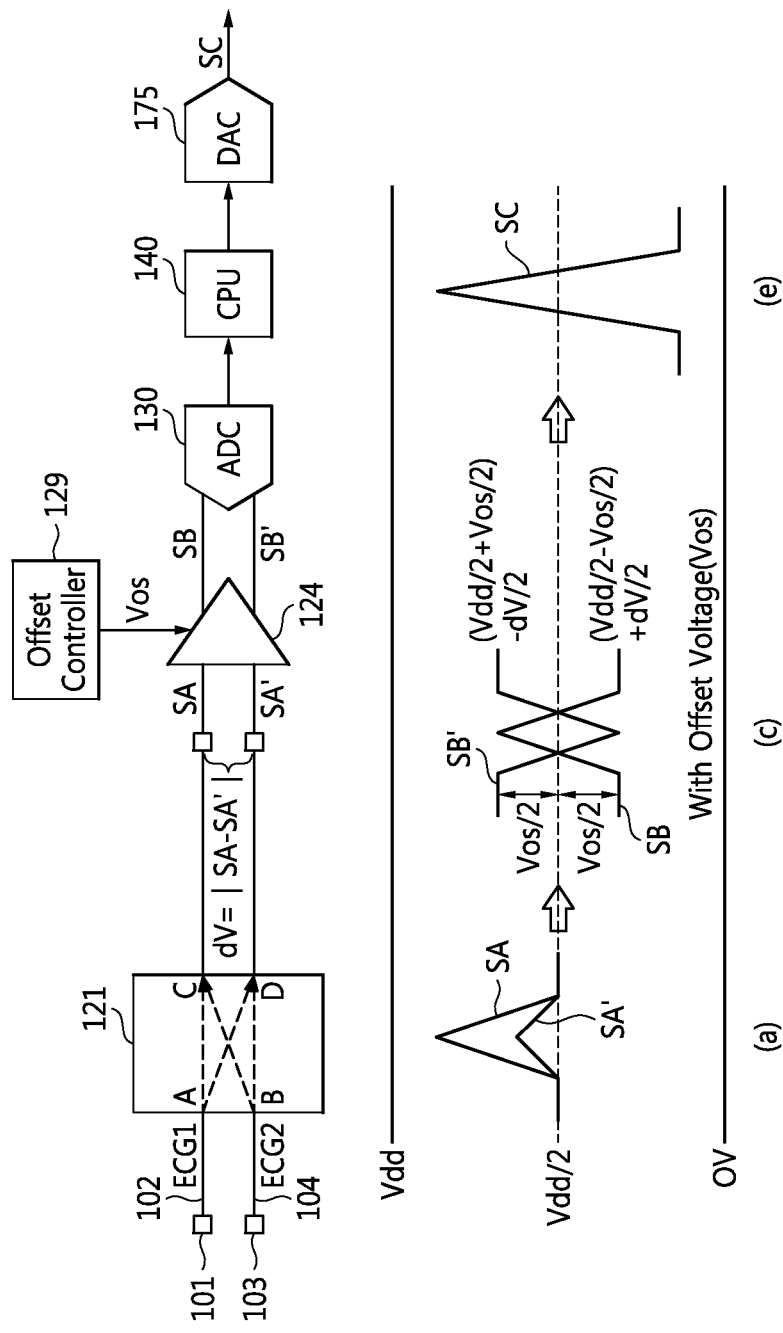

ELECTROCARDIOGRAM (ECG) SENSOR CHIP, SYSTEM ON CHIP (SOC), AND WEARABLE APPLIANCE

CROSS REFERENCE TO RELATED APPLICATION(S)

This application claims priority under 35 U.S.C. 119 from Korean Patent Application No. 10-2014-0160011 filed on Nov. 17, 2014, the subject matter of which is hereby incorporated by reference.

BACKGROUND

Embodiments of the inventive concept relate generally to wearable electronic healthcare appliances and more particularly to electrocardiogram (ECG) sensor chips configured for use in wearable healthcare appliances, systems-on-chip incorporating such ECG sensor chips and related healthcare appliances.

Strong consumer demand for wearable healthcare appliances (hereafter, simply "appliances") capable of monitoring and recording health conditions has followed a growing social emphasis on personal responsibility in health matters. With continued improvements in the miniaturization of electronics, consumers are now able to obtain small, portable devices capable of providing monitoring, recording, and/or displaying a number of health-related conditions. Many of these devices are "wearable" in the sense that they are conveniently configured for use in a manner that allows a user to comfortably wear the device for periods of time.

There are many different characteristics of a person's body that—when properly monitored and interpreted—provide meaningful information regarding the overall health of the person. One important characteristic is the electrical signal(s) associated with operation of the heart. It is well recognized that the heart's electrical activity may be monitored by a set of routine medical tests commonly referred to as an electrocardiogram (ECG).

An ECG may be administered for a variety of reasons including; checking on the overall activity of a heart, identifying the cause of unexplained chest pain like the pain commonly associated with heart attack, pericarditis and angina, identifying the cause certain symptoms commonly associated with heart disease such as shortness of breath, dizziness, fainting and heart palpitations, monitoring the effect of certain medicines on the heart, checking on the operation of mechanical devices implanted in the heart, and defining a health baseline to better monitor chronic health conditions such as high blood pressure, high cholesterol, cigarette smoking and diabetes.

The typical ECG is administered in a doctor's office to a reclining patient by carefully attaching ten (10) electrical leads to designated locations on the patient's body and thereafter recording a set of electrical signals over a period of time. While indisputably useful to medical professionals and harmless to the patient, the typical ECG is far from convenient.

More recently, improved techniques have allowed an ECG-like monitoring of heart-related bioelectrical signals using a wearable device instead of a clumsy set of electrical leads. In this manner, certain aspects of a person's physical condition may be conveniently monitored over longer periods of time outside of a doctor's office. However, such portable devices have heretofore suffered from signal detection problems and significant constrains on acceptable wearable locations of such devices on a person's body. That is, when conventional wearable devices capable of detecting an ECG-like signal are randomly positioned on a person's body the diagnostic results are often disappointing.

SUMMARY

In one aspect, certain embodiments of the inventive concept provide an electrocardiogram (ECG) sensor chip configured for use in a wearable appliance and including; a switch controlled by a switching signal and including a first switch input that receives a first ECG signal, a second switch input that receives a second ECG signal, a first switch output, and a second switch output, an amplifier including a first amplifier input that receives one of the first ECG signal and the second ECG signal from the first switch output and a second amplifier input that receives the other one of the first ECG signal and the second ECG signal from the second switch output, and amplifies a difference between the first ECG signal and second ECG signal, and a location indicator that generates the switching signal in one of a first state and a second state, wherein in response to the first state of the switching signal, the switch passes the first ECG signal from the first switch input to the first switch output and passes the second ECG signal from the second switch input to the second switch output, and in response to the second state of the switching signal, the switch passes the first ECG signal from the first switch input to the second switch output and passes the second ECG signal from the second switch input to the first switch output.

In another aspect, certain embodiments of the inventive concept provide a system configured for use in a wearable appliance, the system including; an electrocardiogram (ECG) sensor chip that receives a first ECG signal from a first ECG sensor and a second ECG signal from a second ECG sensor, and includes an amplifier that amplifies a difference between the first ECG signal and second ECG signal to generate a first ECG output signal and a second ECG output signal, an analog-to-digital converter (ADC) that receives the first and second ECG output signals and generates corresponding ECG digital signals, and a processor that receives the ECG digital signals and processes the ECG digital signals in response to received location information indicating a location of the wearable appliance as worn by a user.

In another aspect, certain embodiments of the inventive concept provide a wearable appliance worn at a location on a user and including; a first electrocardiogram (ECG) electrode, a second ECG electrode, an ECG sensor chip that receives a first ECG signal from the first ECG electrode and a second ECG signal from the second ECG electrode, the ECG sensor chip comprising, a switch controlled by a switching signal and including a first switch input that receives the first ECG signal, a second switch input that receives the second ECG signal, a first switch output, and a second switch output, an amplifier including a first amplifier input that receives one of the first ECG signal and the second ECG signal from the first switch output and a second amplifier input that receives the other one of the first ECG signal and the second ECG signal from the second switch output, and generates an amplified difference signal between the first ECG signal and the second ECG signal, and a location indicator that generates the switching signal in one of a first state and a second state, wherein in response to the first state of the switching signal, the switch passes the first ECG signal from the first switch input to the first switch output and passes the second ECG signal from the second switch input to the second switch output, and in response to the second state of the switching signal, the switch passes the first ECG signal from the first switch input to the second switch output and passes the second ECG signal from the second switch input to the first switch out.

In another aspect, certain embodiments of the inventive concept provide a system on a chip (SoC) including an electrocardiogram (ECG) sensor chip that includes; a switch controlled by a switching signal and including a first switch input that receives a first ECG signal from a first ECG sensor, a second switch input that receives a second ECG signal from a second ECG sensor, a first switch output, and a second switch output, an amplifier including a first amplifier input that receives one of the first ECG signal and the second ECG signal from the first switch output, and a second amplifier input that receives the other one of the first ECG signal and the second ECG signal from the second switch output and generates an amplified difference signal between the first ECG signal and the second ECG signal, and a location indicator that generates the switching signal having one of a first state and a second state, wherein in response to the switching signal having the first state, the switch passes the first ECG signal from the first switch input to the first switch output and passes the second ECG signal from the second switch input to the second switch output, and in response to the switching signal having the second state, the switch passes the first ECG signal from the first switch input to the second switch output and passes the second ECG signal from the second switch input to the first switch out, and an analog-to-digital converter (ADC) that receives the amplified difference signal and generates corresponding ECG digital signals, and a Central Processing Unit (CPU) that receives the ECG digital signals and generates display information that controls generation of a visual image on a display.

In another aspect, certain embodiments of the inventive concept provide a data processing system including; a wearable appliance including the ECG sensor chip, and a computing device configured to communicate information with the wearable appliance via at least one of a wireless connection and a hardwired connection. The wearable appliance includes; a first electrocardiogram (ECG) electrode, a second ECG electrode, and an ECG sensor chip that receives a first ECG signal from the first ECG electrode and a second ECG signal from the second ECG electrode, wherein the ECG sensor chip includes a switch controlled by a switching signal and including a first switch input that receives the first ECG signal, a second switch input that receives the second ECG signal, a first switch output, and a second switch output, an amplifier including a first amplifier input that receives one of the first ECG signal and the second ECG signal from the first switch output and a second amplifier input that receives the other one of the first ECG signal and the second ECG signal from the second switch output, and generates an amplified difference signal between the first ECG signal and the second ECG signal, and a location indicator that generates the switching signal in one of a first state and a second state, wherein in response to the first state of the switching signal, the switch passes the first ECG signal from the first switch input to the first switch output and passes the second ECG signal from the second switch input to the second switch output, and in response to the second state of the switching signal, the switch passes the first ECG signal from the first switch input to the second switch output and passes the second ECG signal from the second switch input to the first switch out.

In another aspect, certain embodiments of the inventive concept provide a method of operating an electrocardiogram (ECG) sensor chip receiving a first ECG signal and a second ECG signal and being incorporated in a wearable appliance worn by a user, the method including; generating a switching signal, using the switching signal to control operation of a switch, wherein in response to the switching signal having a first state, the first ECG signal passes from a first switch input to a first switch output and the second ECG signal passes from a second switch input to a second switch output, else in response to the switching signal having a second state, the first ECG signal passes from the first switch input to the second switch output and the second ECG signal passes from the second switch input to the first switch output, and amplifying a difference between the first ECG signal and the second ECG signal using an amplifier connected to the first switch output and the second switch output.

BRIEF DESCRIPTION OF THE DRAWINGS

The above and other features and advantages of the inventive concept will become more apparent to those skilled in the art upon consideration of certain exemplary embodiments illustrated in the attached drawings, in which:

FIGS. 5, 6A, 6B, 6C and 7 are respective circuit diagrams further illustrating in different examples the ECG sensor chip 120 of FIG. 4;

FIGS. 12A and 12B are conceptual diagrams illustrating the use of voltage offsets in the capture and amplification of an ECG signal according to certain embodiments of the inventive concept;

DETAILED DESCRIPTION

Figure 1:
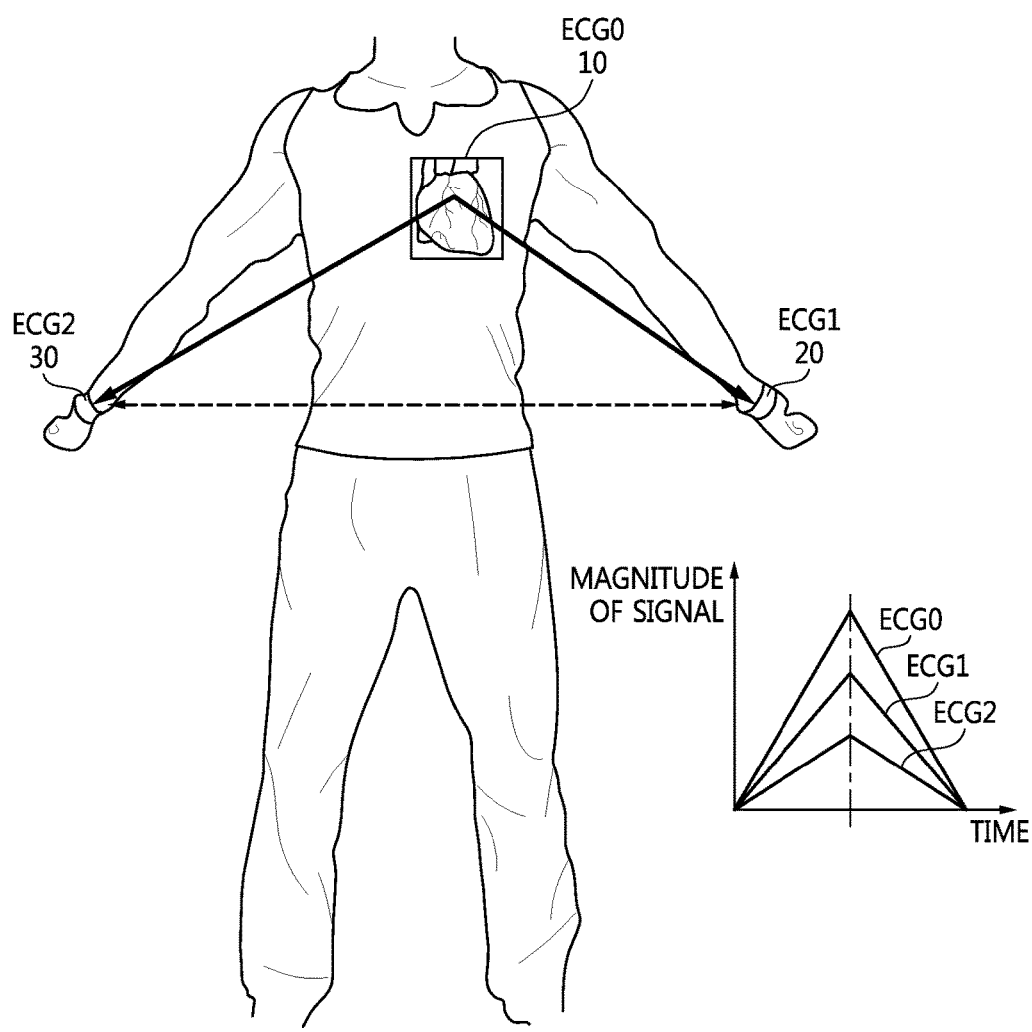
FIG. 1 is a conceptual diagram illustrating the capture of an electrocardiogram (ECG) signal according to embodiments of the inventive concept.

Certain embodiments of the inventive concept will now be described in some additional detail with reference to the accompanying drawings. This inventive concept may, however, be embodied in many different forms and should not be construed as being limited only the illustrated embodiments. Rather, these embodiments are provided so that this disclosure will be thorough and complete, and will fully convey the scope of the invention to those skilled in the art. Throughout the written description and drawings, like reference numbers and labels are used to denote like or similar elements.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. As used herein, the term "and/or" includes any and all combinations of one or more of the associated listed items and may be abbreviated as "/".

It will be understood that, although the terms first, second, etc. may be used herein to describe various elements, these elements should not be limited by these terms. These terms are only used to distinguish one element from another. For example, a first signal could be termed a second signal, and, similarly, a second signal could be termed a first signal without departing from the teachings of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present application, and will not be interpreted in an idealized or overly formal sense unless expressly so defined herein.

The term "wearable appliance" is used hereafter to denote a broad class of user-wearable electronic devices that may be used to detect, capture, monitor and/or record one or more bioelectrical signal(s) associated with the user's body. Wearable appliances will have variety of configurations variously appropriate to different applications and dispositions on the user's body. Certain wearable appliances consistent with the inventive concept will be publicly apparent when worn by a user and will be readily recognizable as common fashion accessories such as a watches, rings, bracelets, anklets, necklaces, headphones, hats, eye glasses, etc. In this regard, certain embodiments of the inventive concept may be physically incorporated within common electrical devices capable of performing their normal function(s), like watches that tell time and headphones that provide audio signals, for example. Other wearable appliances consistent with the inventive concept will be incorporated within articles of clothing such as neckties, wristbands, headbands, shirts, undershirts, bras, etc. Still other wearable appliances consistent with the inventive concept will be more appropriately worn underneath clothing and may take the form of skin-adhering patches of various sizes, shapes and compositions.

FIG. 1 is a conceptual diagram illustrating the capture of a bioelectrical signal associated with the operation of a user's heart. As noted above, this type of signal is routinely captured by an electrocardiogram (ECG) test. Thus, for purposes of the description that follows, this type of signal—in all of its variations and manifestations within the human body and in all of its electrically captureable forms, whether singularly or as a combination—will hereafter be generally referred to as an "ECG signal". Accordingly, in FIG. 1 the capture of an ECG signal is illustrated. In this context, the term "capture" refers to any process that identifies, detects, acquires and/or measures an ECG signal sufficient to generate at least one analog signal, or corresponding digital data, that accurately represents the electrical activity of the user's heart as manifested by an ECG signal.

Under the foregoing definition, a user will only produce a single ECG signal associated with the activity of his/her heart. However, the ECG signal will be differently manifested and differently captured at different locations on the user's body. Ideally, an ECG signal would be captured by one or more ECG sensors placed on appropriate locations directly proximate the user's heart (e.g., a first location 10 in FIG. 1 capturing a first ECG signal ECG0). Unfortunately, while the first location 10 centered over the user's heart provides the strongest (i.e., highest differential amplitude) ECG signal, it is not necessarily convenient and the disposition of sensors at this location may be uncomfortable to the user during physical exercise. Accordingly, it is often highly desirable for the user of a wearable appliance to be able to place the constituent ECG sensors on a more convenient location of his/her body, such as a wrist.

This dispositional flexibility is one feature sadly lacking in many conventional devices. Such conventional devices routinely mandate an exact disposition location and any departure from this location greatly impairs an accurate ECG signal capture. In contrast, wearable appliances according to the inventive concept recognize that an ECG signal will be differently manifested when captured at different locations on a user's body. However, wearable appliances according to the inventive concept nonetheless provide a user with the flexibility of wear the wearable appliance at a location deemed most comfortable or most convenient to the user.

For example with reference to FIG. 1, certain aspects of the inventive concept recognize that a second ECG signal (ECG1) apparent at a second location 20 (i.e., the user's left wrist) will be less strong than the first ECG signal (ECG0) at the first location 10, and that a third ECG signal (ECG2) apparent at a third location 30 (i.e., the user's right wrist) will be less strong than the second ECG signal (ECG1). That is, the inventive concept recognizes that increasing the distance between an ECG signal capture location on a user's body and the user's heart tends to decrease the input signal-to-noise ratio (SNR) of the captured ECG signal. Nonetheless, embodiments of the inventive concept are configured in such a manner that allow a user to reasonably wear a wearable appliance at multiple desirable locations on his/her body.

Figure 2C:
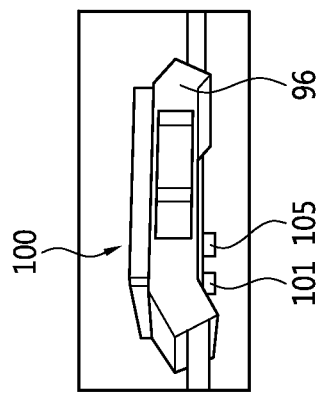
FIG. 2, inclusive of FIGS. 2A, 2B and 2C, is a perspective diagram illustrating in one example a wearable appliance capable of capturing an ECG signal according to embodiments of the inventive concept.
Figure 2B:
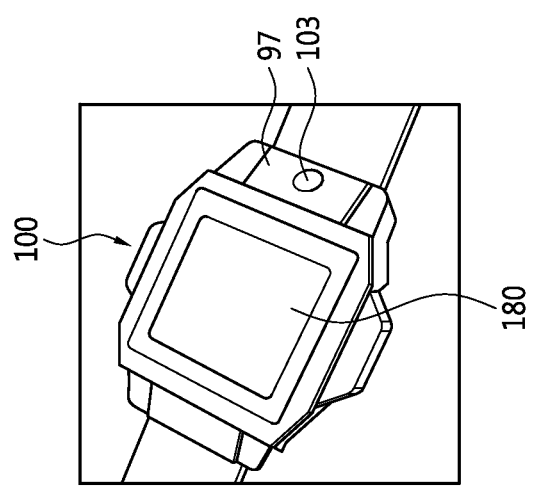
Figure 2A:
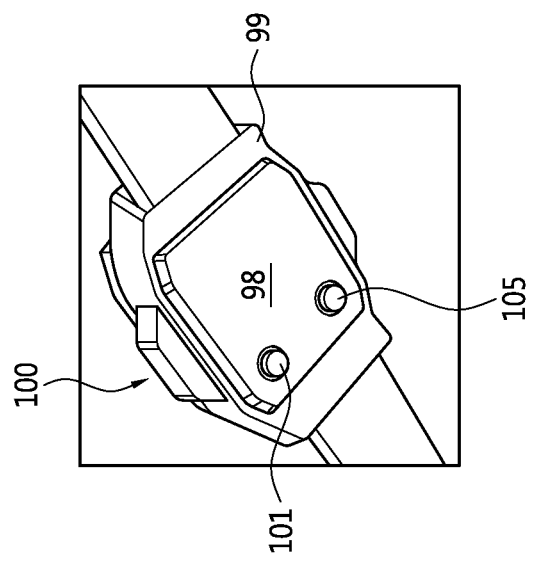

FIG. 2, inclusive of FIGS. 2A, 2B and 2C, is a set of perspective diagrams illustrating a wearable appliance 100 capable of capturing and processing an ECG signal according to certain embodiments of the inventive concept. Although the wearable appliance 100 shown in FIG. 2 is a watch, those of ordinary skill in the art will recognize that this is merely one convenient example, and wearable appliances consistent with the inventive concept may take many different forms.

The wearable appliance 100 of FIG. 2 comprises a watch body 99 housing circuitry and/or software used to implement the functionality of the wearable appliance 100, as well as circuitry and/or software used to provide typical watch functionality. A first ECG electrode 101 and a ground electrode 105 protrude from a bottom surface 98 of the watch body 99. When normally worn by a user at a desired location, such as a left or right wrist, the bottom surface 98 of the watch body 99. Hence, the protruding first ECG electrode 101 and ground electrode 105 are placed in direct contact with the user's skin when the wearable appliance 100 is worn by the user. This direct skin contact is highly beneficial to the capture of an ECG signal by the watch 100. In contrast, a second ECG electrode 103 may be disposed on a top surface 97 of the watch body 99 opposing the bottom surface 98. Alternately, the second ECG electrode 103 may be disposed on a side surface 96 of the watch body 99. When normally worn by a user, the top surface 97 and side surfaces 96 of the watch body 99, along with the second ECG electrode 103 are readily accessible to the user. In the embodiment illustrated in FIG. 2, the first ECG electrode 101 may be designated a positive electrode, and the second ECG electrode 103 may be designated a negative electrode.

In this context, the term "ECG sensor" refers to any one of a number of different bioelectrical, electro-mechanical, and/or electrical components capable of capturing an ECG signal when placed proximate to or directly in contact with the user's body.

Although in FIG. 2, the ground electrode 105 is disposed on the bottom surface 98 of the body 99 proximate the first ECG electrode 101, other embodiments of the inventive concept may differently place the ground electrode 105, or completely omit it. However, the use of the ground electrode 105 may significantly aid in ECG signal synchronization between the wearable appliance 100 and the user. That is, use of the ground electrode 105 prevents floating of the ECG signal during capture of the ECG signal by an ECG sensor chip included in the wearable appliance 100. As a result, the combination of various ECG sensors and the ECG sensor chip in the wearable appliance 100 may be more reliably operated.

Figure 3A:
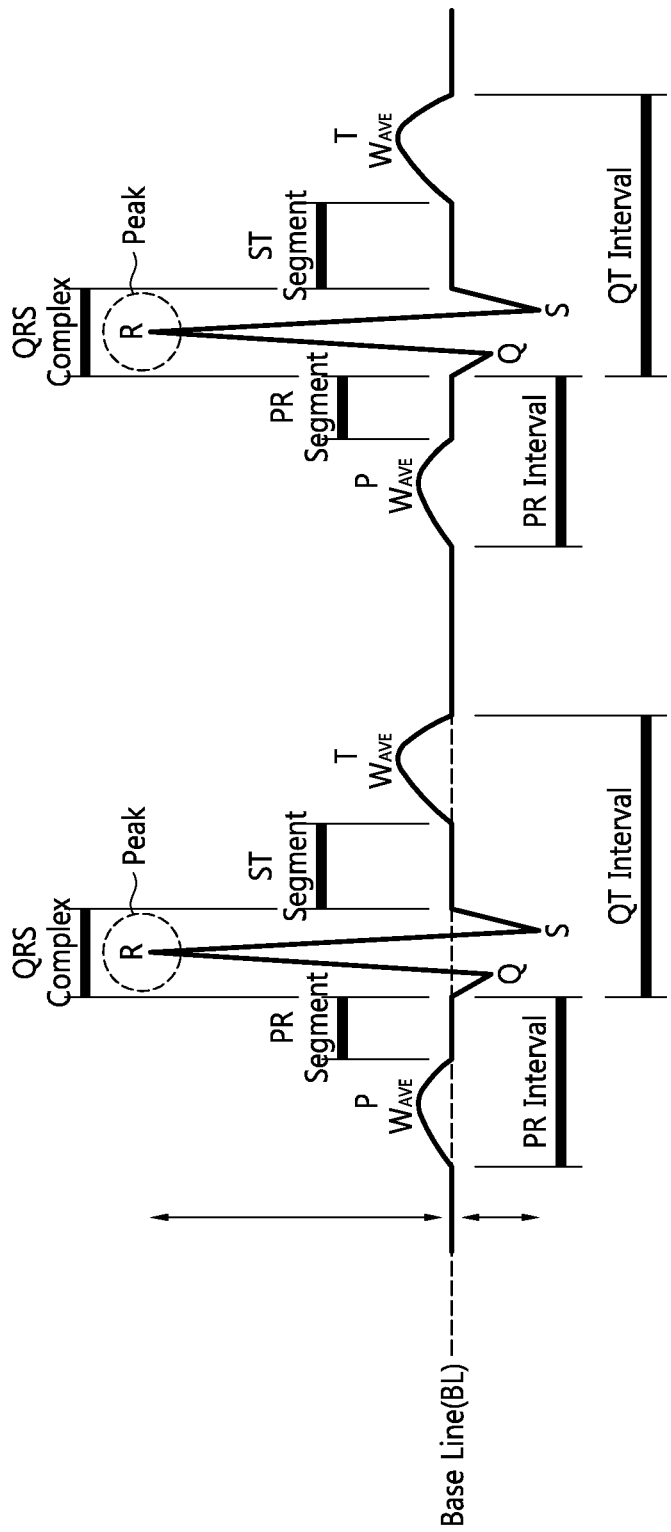
FIG. 3, inclusive of FIGS. 3A and 3B, is a set of comparative waveform diagrams further illustrating the capture of an ECG signal using a wearable appliance like the one shown in FIG. 2.
Figure 3B:
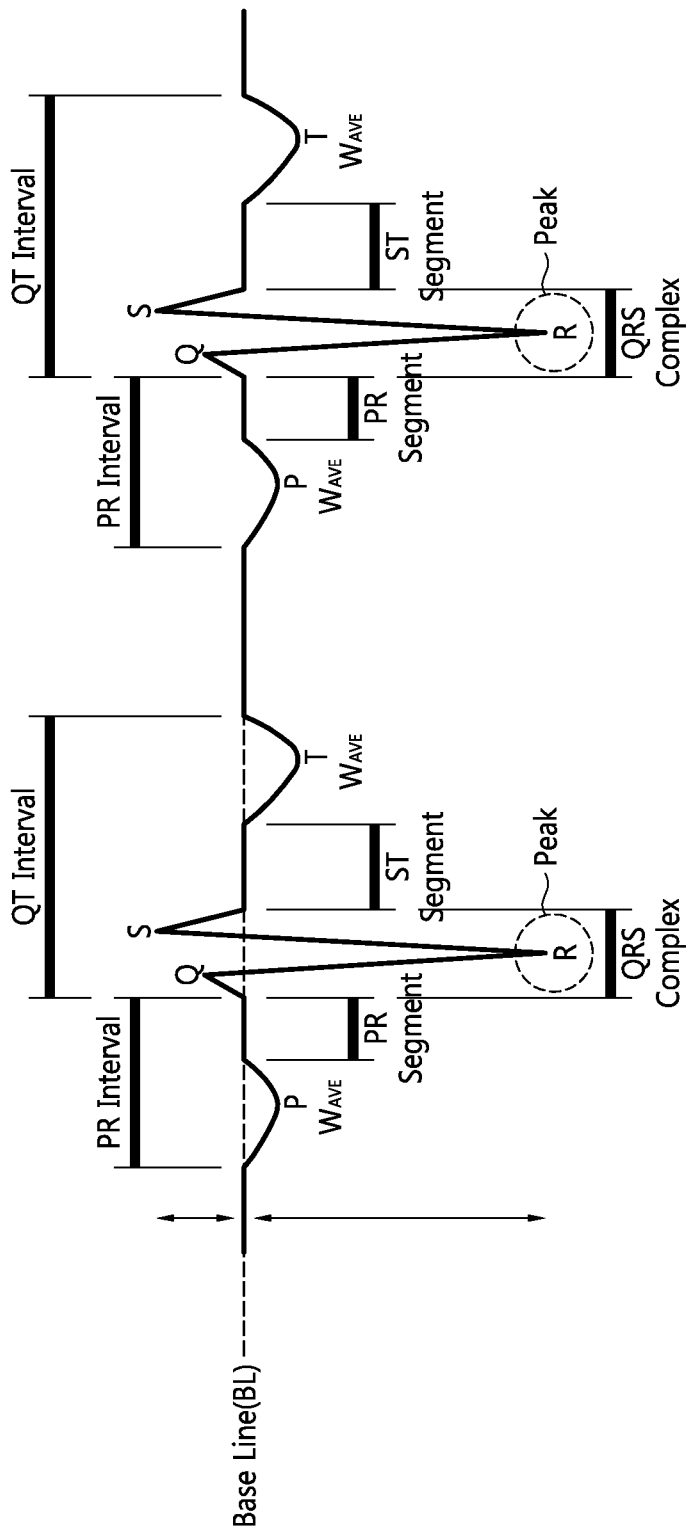

FIG. 3, inclusive of FIGS. 3A and 3B, further illustrates the typical nature of an ECG signal being variously captured by the wearable appliance 100 of FIG. 2. Referring to FIGS. 1, 2, and 3A, an ECG signal having the waveform shown in FIG. 3A may be captured by an ECG sensor chip of the watch-type wearable appliance 100 when worn on the left wrist of the user (location 20 in FIG. 1), and when the second ECG electrode 103 is depressed by the user using a finger of his/her right hand (location 30 in FIG. 1). In other words, when the second ECG electrode 103 contacts the finger of the right hand, the first electrode 101 and ground electrode 105 are placed in contact with the skin of the user's left wrist.

Of particular note with respect to the ECG signal waveform shown in FIG. 3A, a positive ECG signal peak ("R") is periodically manifest above the ECG signal baseline. Of course, the polarity (positive or negative) of ECG signal peak above or below the ECG signal baseline is a matter of definition for the ECG sensor chip of the wearable appliance 100.

Referring now to FIGS. 1, 2, and 3B, the ECG signal having the waveform shown in FIG. 3B may be captured by an ECG sensor chip of the watch-type wearable appliance 100 when worn on the right wrist of the user (location 30 in FIG. 1), and when the second ECG electrode 103 is depressed by the user using a finger of his/her left hand (location 20 in FIG. 1). In other words, when the second ECG electrode 103 contacts the finger of the left hand, the first electrode 101 and ground electrode 105 are placed in contact with the skin of the user's right wrist.

Of particular note with respect to the ECG signal waveform shown in FIG. 3B, a negative ECG signal peak ("R") is periodically manifest below the ECG signal baseline. More importantly, the absolute value of the difference between the ECG baseline and the ECG signal peak captured at the right wrist may be less than the absolute value of the difference between the ECG baseline and the ECG signal peak captured at the left wrist. Therefore, all other things remaining equal, the ECG signal apparent at the right wrist may be more difficult to accurately capture than the ECG signal apparent at the left wrist. As a result, more signal processing time and resources may be required from the ECG sensor chip when the wearable appliance 100 of FIG. 2 is worn on a user's right wrist, or some other location manifesting a relatively weaker version of the ECG signal.

Figure 4:
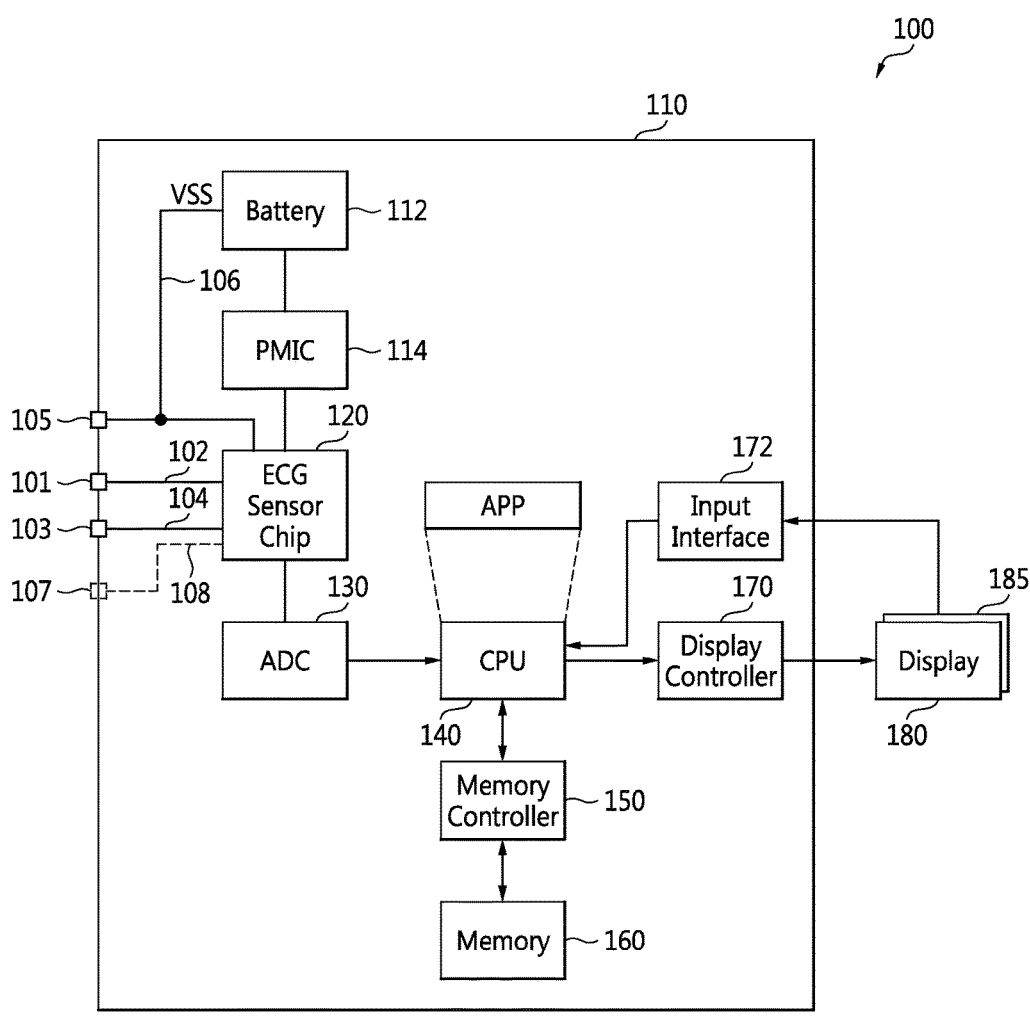
FIG. 4 is a block diagram illustrating a wearable appliance according to certain embodiments of the inventive concept.

FIG. 4 is a block diagram further illustrating in one example the wearable appliance 100 of FIG. 2. Here, the wearable appliance 100 generally comprises a processing unit 110 and a display 180. The display 180 is an optional component, but may prove very useful in certain embodiments of the inventive concept, such as the watch-wearable appliance 100 of FIG. 2.

The processing unit 110 may be used to receive, capture and process an ECG signal and to control the operation of the display 180 some other external circuitry responsive to the ECG signal. The processing unit 110 may alternately or additionally be used to derive a control signal from the captured ECG signal, where this control signal may be provided to one or more external circuits.

The processing unit 110 of FIG. 4 includes a first signal port (e.g., a pad, terminal or similar electrical element) receiving a first ECG signal from the first ECG electrode 101, a second signal port receiving a second ECG signal from the second ECG electrode 103, a third signal port receiving a ground signal from the ground electrode 105. In addition, the processing unit 110 of FIG. 4 includes a battery 112, a power management integrated circuit (PMIC) 114, an ECG sensor chip 120, an analog-to-digital converter (ADC) 130, a central processing unit (CPU) 140, a memory controller 150, a memory 160, a display controller 170, and an input interface 172.

Optionally, the processing unit 110 may also include a fourth signal port configured to receive a location signal provided by (e.g.,) a user-activated, location input element 107 discussed in further detail hereafter.

Assuming for purposes of this description that the wearable appliance 100 of FIG. 4 is similar to the wearable appliance of FIG. 2, it is further assumed that the first ECG electrode 101 and the ground electrode 105 may commonly be placed in contact with either the left wrist or the right wrist of the user, and that the second ECG electrode 103 is placed in contact with the right hand or the left hand of the user, respectively. Under these assumed conditions, the first ECG signal is provided to the processing unit 110 via the first signal port, the second ECG signal is provided to the processing unit 110 via the second signal port, and the ground signal is provided to the processing unit 110 via the third signal port.

The first signal port is connected to the ECG sensor chip 120 via a first signal line 102, the second signal port is connected to the ECG sensor chip 120 via a second signal line 104, and the third signal port is connected to the battery 112 via a third signal line 106. In this regard, a ground voltage (VSS) may be communicated to one or more of the processing unit 110 components, such as the PMIC 114, ECG sensor chip 120, ADC 130, CPU 140, memory controller 150, memory 160, display controller 170, and/or input interface 172.

In combination, the battery 112 and PMIC 114 may be used to provide one or more power voltages (not shown) to the processing unit 110 components, display 180, and/or input device 185.

The ECG sensor chip 120 may be used to receive and process the first ECG signal and the second ECG signal in order to generate one or more ECG output signal(s). For example, the ECG sensor chip 120 may be used to amplify a voltage difference between the first and second ECG signals in order to generate a corresponding, amplified ECG output signal(s).

Assuming that the ECG output signal(s) are analog in nature, the ADC 130 may be used to receive the ECG output signal(s) and convert the ECG output signal(s) into one or more corresponding ECG digital signal(s). In this regard, certain embodiments of the inventive concept use differential, first and second ECG output signals provided from the ECG sensor chip 120, received by the ADC 130, and then respectively used by the ADC 130 to generate respective first and second ECG digital signals. Thereafter, the first and second ECG digital signals may be provided to the CPU 140.

The CPU 140 may be used to control the overall operation of all processing unit 110 components, as well as the display 180 and user input device 185. In response to one or more ECG digital signals provided by the ADC 130, the CPU 140 may perform one or data processing routines adapted to calculate, for example, the user's heart rate. Alternately or additionally, the CPU 140 may be used to identify an arrhythmia or irregular heartbeat for the user. Such data processing routines may be controlled by one or more applications (APP) running on the CPU 140. The programming code used to implement such applications, wholly or in part, may be stored in the memory 160. Regardless of the particular data processing routines run in relation to the ECG digital signal(s) received from the ADC 130 by the CPU 140, the CPU 140 may provide corresponding control signal(s) and/or data (hereafter, control signal/data") to the display controller 170.

In one exemplary data processing routine, an application running on the CPU 140 may be used to count over a defined period of time a number of ECG peaks identified in one or more ECG signal(s). (See, e.g., FIG. 3). The counted number of ECG peaks may be used to calculate the user's heart rate, and corresponding control signal/data may be communicated from the CPU 140 to the display controller 170 in response to this calculation.

In another exemplary data processing routine, an application running on the CPU 140 may be used to calculate a time interval between sequential ECG peaks identified in one or more ECG signal(s). The calculated interval may be used to identify an arrhythmia, and corresponding control signal/data may be communicated to the display controller 170 in response to this calculation.

The memory 160 may be used to store ECG digital signals received from the ADC 130, intermediate computational data generated by an application running on the CPU 140, and/or control signal/data provided by the CPU 140 to the display controller 170.

Thus, the ECG digital signals, which may be respectively or collectively derived from one or more analog ECG signal(s) received by the ECG sensor chip 120, may be variously processed by the CPU 140 under the control of one or more application(s). For example, assuming the provision of multiple ECG digital signals, the CPU 140 may invert one or more of the ECG digital signal(s) for use during a subsequent data processing routine.

Exemplary configurations for the ECG sensor chip 120 of FIG. 4 are illustrated in FIGS. 5, 6, 7, 9, 10, and 11.

The memory controller 150 may be used to write data received from the CPU 140 to the memory 160 and/or read data from the memory 160. The memory 160 may be configured from volatile and/or non-volatile memory. Volatile memory may be random access memory (RAM), dynamic RAM (DRAM), or static RAM (SRAM). Non-volatile memory may be electrically erasable programmable read-only memory (EEPROM), flash memory, magnetic RAM (MRAM), spin-transfer torque MRAM, ferroelectric RAM (FeRAM), phase-change RAM (PRAM), or resistive RAM (RRAM). The memory 160 may be implemented as a smart card, a secure digital (SD) card, a multimedia card (MMC), an embedded MMC (eMMC), an embedded multi-chip package (eMCP), a perfect page NAND (PPN), a universal flash storage (UFS), a solid state drive (SSD), or an embedded SSD (eSSD). The memory 160 may also be implemented as fixed memory or removable memory.

Although a single memory controller 150 and memory 160 are shown in FIG. 4 for clarity of the description, the memory 160 may include a number of separately or collectively implemented memory device controlled by one or more the memory controller(s) 150, where such memory devices may be similar or different in their operational nature and/or configuration.

As noted above, the display controller 170 receives certain control signal/data from the CPU 140 and controls the operation of the display 180 according to one or more conventionally understood interfaces. Thus, display controller 170 may be used to control the generation and display of visual images related to the control signals and/or data provided by the CPU 140 under the control of (e.g.,) firmware executed by the CPU 140.

Figure 8:
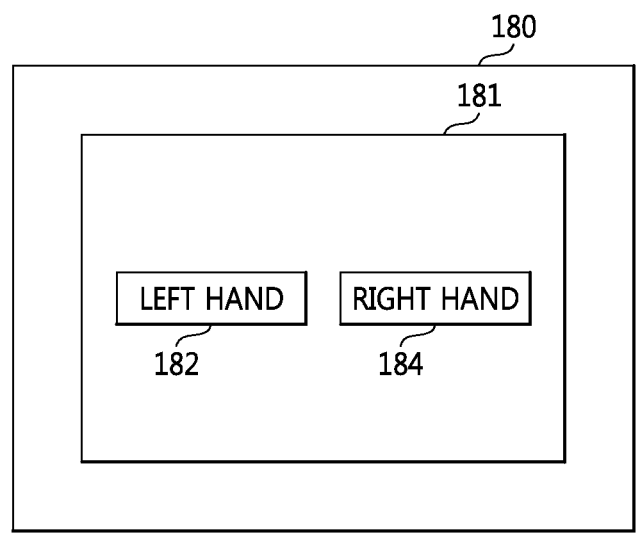
FIG. 8 is a diagram illustrating a graphical user interface (GUI) that may be displayed by a display incorporated in a wearable appliance according to certain embodiments of the inventive concept.

The input interface 172 may be used to communicate data input via the user input device 185 and/or display 180 to the CPU 140. The user input device 185 may be a device, such as a touch screen controller, a touch sensor, or touch pad capable of generating various input signals (or data) controlling the operation of the wearable appliance 100. In certain embodiments of the inventive concept, the user input device 185 will be a graphical user interface (GUI) displayed on the display 180. FIG. 8 shows one example of a user-interactive GUI that may be displayed on a display 180. The CPU 140 may be used to receive user input signals and/or data provided by the user input device 185 via input interface 172. One or more applications (APP) may be programmed or controlled to in response to such user input signals and/or data.

In certain embodiments of the inventive concept, it may prove advantageous to implement the processing unit 110 of FIG. 4, or some sub-set of the processing unit 110 components, as a single integrated circuit (IC) chip of the form commonly referred to as a System on Chip (SoC). In one example, the ECG sensor chip 120, PMIC 114, ADC130 and CPU 140 may be implemented as a SoC. Alternately, the memory controller 150 and memory 160 may be added to the ECG sensor chip 120, PMIC 114, ADC130 and CPU 140 when implemented as a SoC. In this regard, the memory 160 may be implemented as a SRAM, a DRAM, a small-capacity flash memory, or a large-capacity flash memory in the SoC.

When the memory controller 150 and memory 160 are integrated into a single semiconductor package, the SoC need not include these commonly provided components. Rather, a first semiconductor package including the SoC, and a second semiconductor package including the memory controller 150 and memory 160 may be variously stacked one on top of the other using (e.g.,) stack balls attached or bonded to a printed circuit board (PCB). The first package and second package may be configured using a package on package (PoP) technique in this regard.

Figure 5:
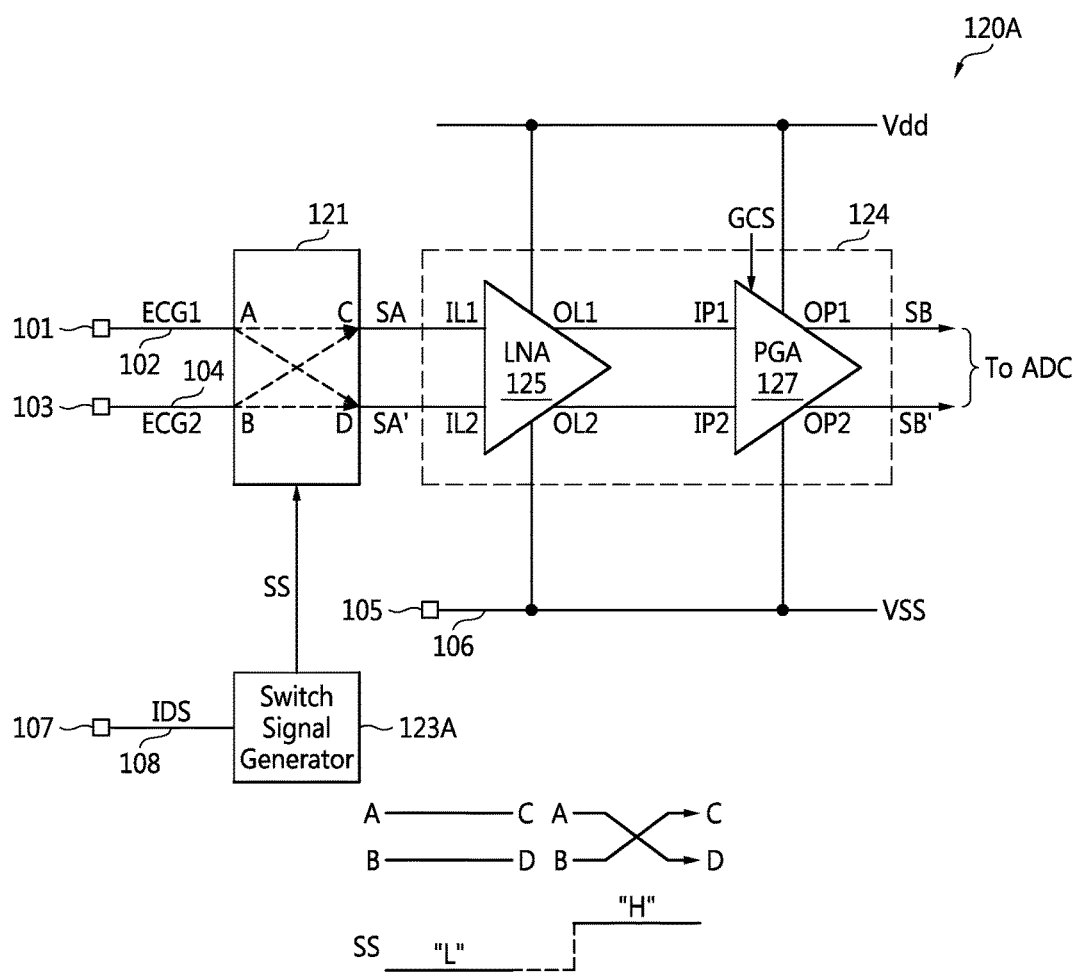

FIG. 5 is a block diagram further illustrating in one example (120A) the ECG sensor chip 120 of FIG. 4. Referring collectively to FIGS. 1, 2, 3, 4 and 5, the ECG sensor chip 120A includes a switch circuit 121, a switch signal generator 123A, and a differential amplifier 124.

The location input element 107 of FIG. 5 is assumed to be a mechanical button according to certain embodiments of the inventive concept. When appropriately activated by the user, the button 107 provides an "location indication signal" (IDS) to the switch signal generator 123A. For example, again assuming the watch-wearable appliance 100 of FIG. 2, the button 107 may be provided on the watch body 99 in a manner that allows the left hand or right hand of the user to operate it when the watch 100 is worn on the opposing right wrist or left wrist. Further, with this assumption, the switch circuit 121 will receive the first ECG signal (ECG1) from the first ECG electrode 101 via the first signal line 102, and will also receive the second ECG signal (ECG2) from the second electrode 103 via the second signal line 104.

In the ECG sensor chip 120A of FIG. 5, the switch signal generator 123A is assumed to generate a switch signal (SS) having at a first (e.g., a logical "low") level (or "first state") in response to a positive indication signal. In response to the switch signal having the first level, the switch circuit 121 operates to apply the first ECG signal received at a first switch input A to a first switch output C, and to apply the second ECG signal received at a second switch input B to a second switch output D. The switch signal generator 123A is further assumed to generate the switch signal having at a second (e.g., a logical "high") level (or "second state") in response to a negative indication signal. In response to the switch signal having the second level, the switch circuit 121 operates to apply the first ECG signal received at the first switch input A to the second switch output D, and to apply the second ECG signal received at the second switch input B to the first switch output C.

The definition of positive/negative indication signals with respect to the user operation of the location input element (e.g., button) 107 is a matter of design choice. Various types and forms of buttons may be used, and may be variously activated/deactivated (e.g., pressed down, pulled up, toggled, turned or touched) by a user.

For example, assuming the use or the watch-wearable appliance 100 described in relation to FIG. 2, when the user chooses to wear the watch 100 on his/her left wrist and therefore leaves the button 107 deactivated per the instructions provided with the watch 100, the deactivated state of the button 107 generates the positive indication signal that is applied to the switch signal generator 123A via the signal line 108. In contrast, when the user chooses to wear the watch 100 on his/her right wrist and therefore activates the button 107, the activated state of the button 107 generates the negative indication signal that is applied to the switch signal generator 123A via the signal line 108. Then, the switch signal generator 123A may response as described above to switch or not-switch the first and second ECG signals.

The differential amplifier 124 receives and amplifies the first and second ECG signals (SA and SA') respectively provided at the first and second switch outputs C and D of the switch circuit 121, and communicates amplified differential signals SB and SB' to the ADC 130. The differential amplifier 124 will preferably have a low noise characteristic and a high amplification factor. Accordingly, in the example of FIG. 5, the differential amplifier 124 is assumed to include a (front-end) low noise amplifier (LNA) 125 and a (back-end) programmable gain amplifier (PGA) 127. In this regard, an operating voltage Vdd and ground voltage VSS are applied to the LNA 125 and PGA 127 as operating voltages.

The LNA 125 may be used to initially (or intermediately) amplify a difference between the first and second ECG signals received via respective LNA inputs IL1 and IL2 and to respectively provide amplified first and second ECG signals (e.g., first and second differential signals) at LNA outputs OL1 and OL2. The PGA 127 may then be used to further amplify the difference between the first and second ECG signals received via respective PGA inputs IP1 and IP2 in response to an input gain control signal (GCS), and to respectively provide further amplified first and second ECG signals at PGA outputs OP1 and OP2.

In this manner, the ECG sensor chip 120A of FIG. 5 is able to process ECG signal(s) no matter the location (e.g., left wrist/right wrist of a user) from which the ECG signal(s) are acquired by the wearable appliance 100 in response to the user's operation of a location input element. Of course, the watch-wearable appliance 100 example drawn in relation to left/right wrists of a user is only one example. Differently configured wearable appliances according to embodiments of the inventive concept may be differently located and will incorporate an appropriate location input element.

Figure 6B:
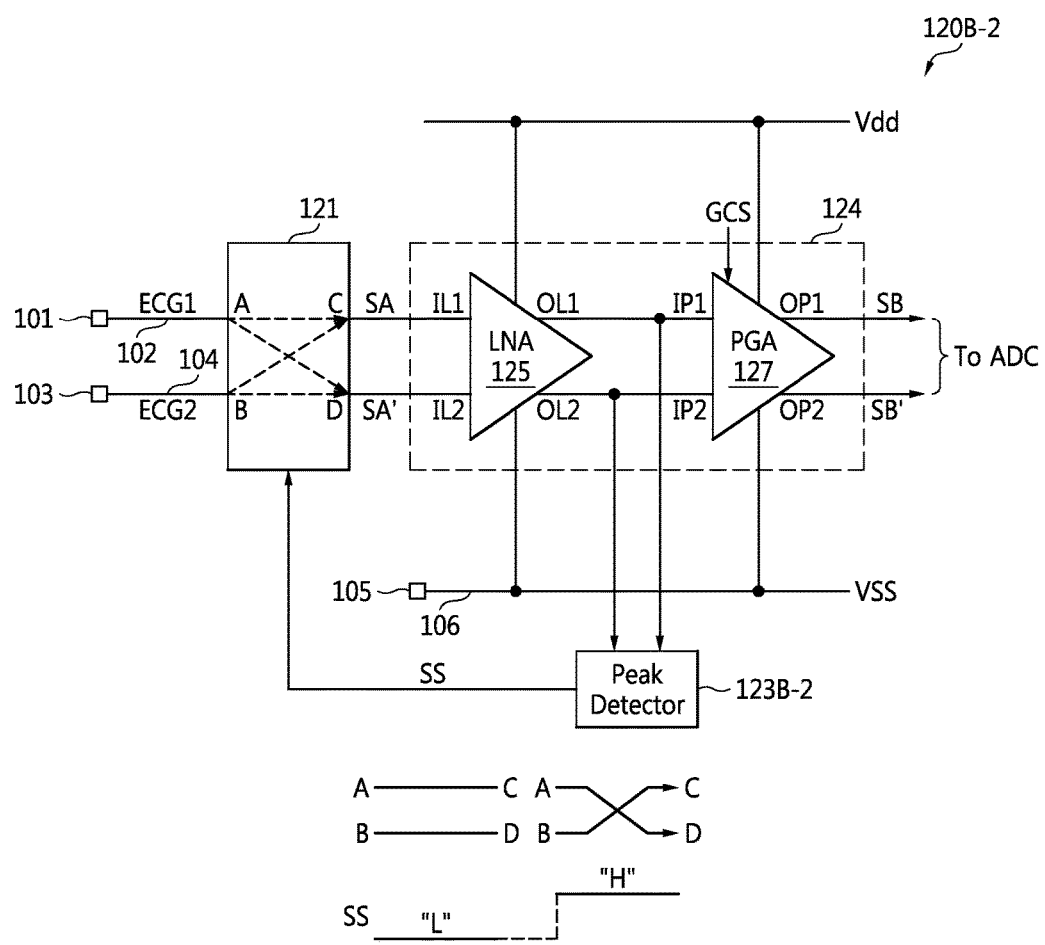
Figure 6C:
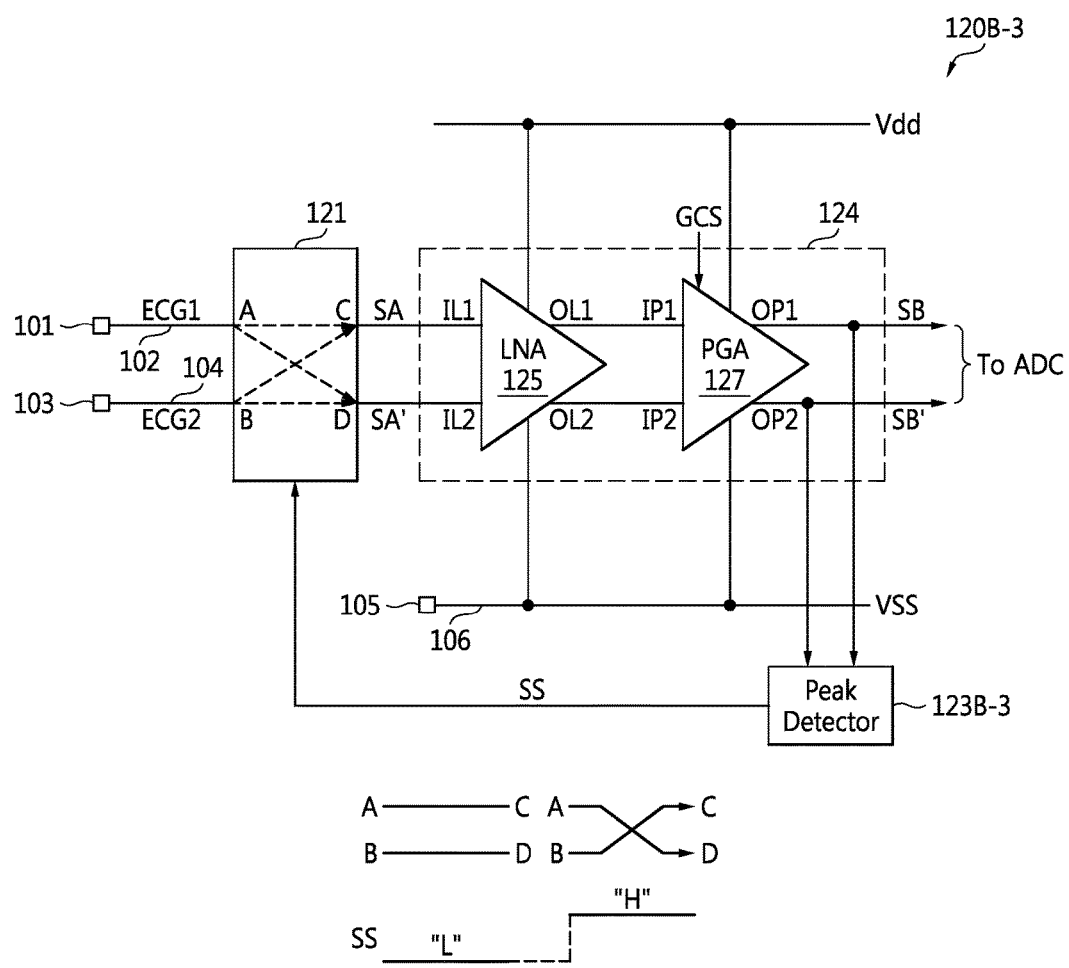

FIG. 6 is a block diagram further illustrating in another example (120B) the ECG sensor chip 120 of FIG. 4. Referring to FIGS. 1, 2, 3, 4, 5 and 6, the ECG sensor chip 120B again includes the switch circuit 121 and differential amplifier 124 previously described in relation to the embodiment illustrated in FIG. 5. Accordingly, these elements and their related signals will not be described in relation to FIG. 6.

However, the ECG sensor chip 120B of FIG. 6 includes a different type of "location indicator" as compared with the ECG sensor chip 120A described in relation to FIG. 5. Namely, instead of using a switch signal generator 123A responsive to an indication signal (IDS) generated by a location input element (e.g., button 107) activated/deactivated by the user, the switch signal (SS) applied in the ECG sensor chip 102B of FIG. 6 is generated by a peak detector 123B.

Notably, the peak detector 123B used in the ECG sensor chip 120B of FIG. 6 is an example of a switch signal generating unit that "automatically" provides the switching signal based on the nature of the received ECG signal(s). By way of comparison, the combination of switch signal generator 123A and button 107 are used in the ECG sensor chip 120A of FIG. 5 is an example of a switch signal generating unit that "manually" provides the switching signal.

It is assumed for purposes of this description that the peak detector 123B generates the switch signal having the first level by operational default. Thus, again assuming the watch-wearable appliance 100 example of FIG. 2, when a user wears the watch 100 on his/her left wrist and touches the second electrode 103 with his/her right hand, the resulting first and second ECG signals (see FIG. 3) will be automatically detected at the LNA outputs OL1 and OL2, or alternately at the PGA outputs OP1 and OP2. Upon detection of the first and second ECG signals by the peak detector 123B, the respective waveforms (or aspects of the waveforms, like the ECG peak) will be interrupted to indirectly determine the location of the watch-wearable appliance as worn by the user.

Thus, when a relatively stronger first ECG signal apparent at the first LNA output OL1 is detected in relation to a relatively weaker second ECG signal apparent at the second LNA output OL2, the peak detector interrupts this result as the watch 100 being worn on the left wrist and generates the switching signal having the first level (i.e., the default option). In contrast, when a relatively weaker first ECG signal apparent at the first LNA output OL1 is detected in relation to a relatively stronger second ECG signal apparent at the second LNA output OL2, the peak detector interrupts this result as the watch 100 being worn on the right wrist and generates the switching signal having the second level.

Here, the switch 121 operates as previously described in relation to the switching signal (SS).

Thus, in certain embodiments of the inventive concept, the peak detector 123B may be used to determine whether at least one ECG peak in amplified, first and second ECG signals respectively apparent at outputs of the LNA 125 or PGA 127 is above or below the ECG signal baseline. In response to this determination, the peak detector 123B may be used to generate the switch signal having an appropriate level. That is, when at least one of the ECG peaks of the amplified, first and second ECG signals is detected above the baseline as shown in FIG. 3A, the peak detector 123B will generate the switch signal with the first level. However, when at least one of the ECG peaks of the amplified, first and second ECG signals is detected below the baseline as shown in FIG. 3B, the peak detector 123B will generate the switch signal with the second level.

Here again, an ECG sensor chip 120B according to certain embodiments of the inventive concept correctly processes received ECG signal(s) regardless of the location (e.g., left/right wrist) that the user decides to wear the wearable appliance acquiring the ECG signal(s).

Although the peak detector 123B of FIG. 6 is illustrated as detecting amplified first and second ECG signals apparent at the respective outputs of the LNA 125 (or the PGA 127), the first and second ECG signals apparent at the switch circuit 121 may be detected in other embodiment of the inventive concept.

Figure 7:
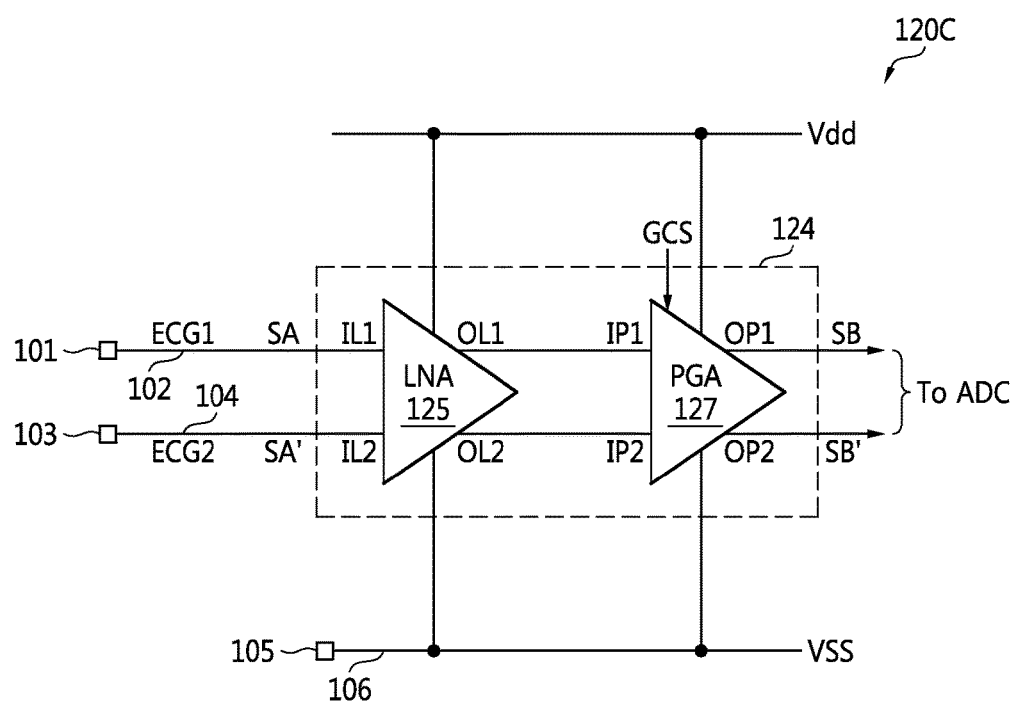

FIG. 7 is a block diagram further illustrating in still another example (120C) the ECG sensor chip 120 of FIG. 4. Referring to FIGS. 1, 2, 3, 4 and 7, the ECG sensor chip 120C substantially includes only the differential amplifier 124, as compared with the previous two exemplary embodiments.

In the absence of a switch 121, the LNA 125 of FIG. 7 may directly receive the first ECG signal via the first signal line 102 and the second ECG signal via the second signal line 104. Following amplification of a voltage difference between these two ECG signals as previously described, the first and second ECG output signals respectively apparent at the first and second PGA outputs OP1 and OP2, are communicated to the ADC 130, and the processing and interruption of these ECG output signals is left to the CPU 140 based on location information identifying a location at which the user wears the wearable appliance. For example, CPU processing and interpretation of ECG digital signals derived from the first and second ECG signals may be performed without user-provided input (automatically) or with user-provided input, such as location information input via the user input device 185 or a GUI displayed on the display 180.

Referring again to FIGS. 4, 7 and 8, the GUI 181 displayed on display 180 may be created by an application (APP) running on the CPU 140. Again assuming the watch-wearable appliance 100 of FIG. 2, the user may be asked to indicate as part of an application execution via the GUI 181 the location of the watch 100 (e.g., on the left or right wrist) as worn by the user.

Such an indication may be easily made by selecting and touching one of the GUI icons 182 or 184 displayed on the display 180. Thereafter, the input device 185 may be used to communicate location indication data (e.g., a sensed touch signal) to the CPU 140 via the input interface 172. The CPU 140 may then be used to appropriately process (e.g.,) the ECG output signals provided to the CPU 140 by the ADC 130 and associated with the first and second ECG signals, whether the first and second ECG signals are presented to the amplifier 124 as shown in FIG. 3B or as shown in FIG. 3A.

Of further note, the foregoing selection by the user between the GUI icons 182 and 184 may occur either before, or after the first and second ECG signals are received by the amplifier 124.

Thus, it has been shown with reference to the embodiments respectively illustrated in FIGS. 5, 6 and 7 that an ECG sensor chip of various designs may be used to determine (or respond to) the location of a wearable appliance, and process ECG signal(s) captured by the wearable appliance regardless of the location. This wearable appliance location determination and subsequent ECG signal processing capabilities may be implemented using manual or automatic detection approaches, and may be implemented using hardware-based and/or software-based solutions.

Figure 9:
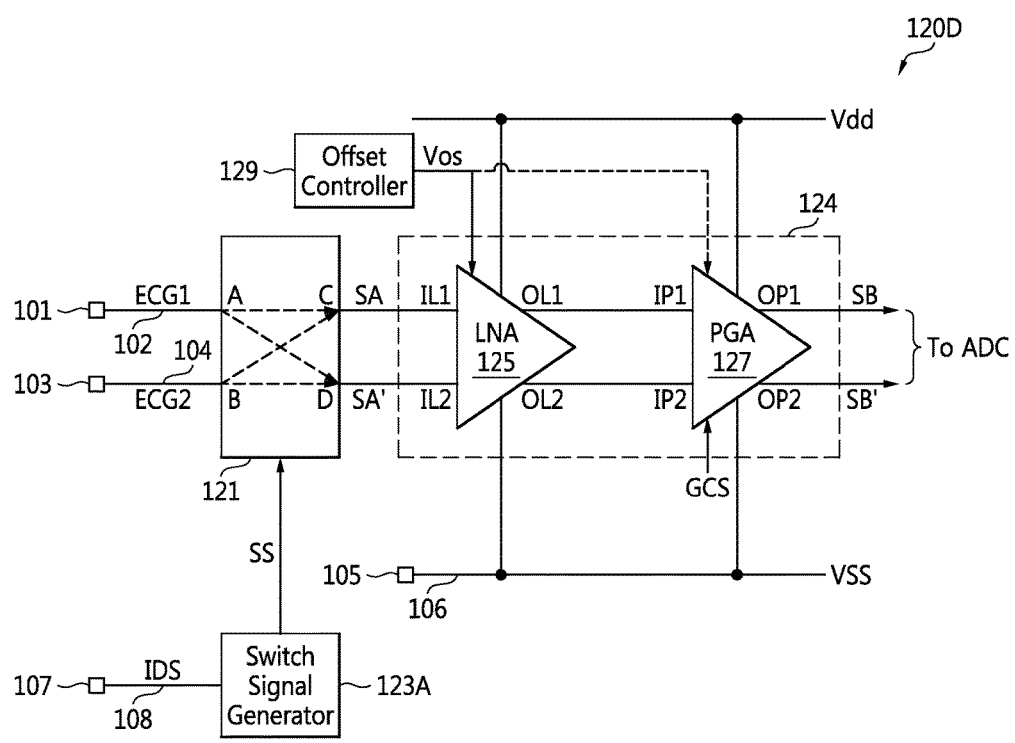
FIGS. 9, 10A, 10B, 10C and 11 are respective circuit diagrams further illustrating in different examples the ECG sensor chip 120 of FIG. 4.
Figure 10A:
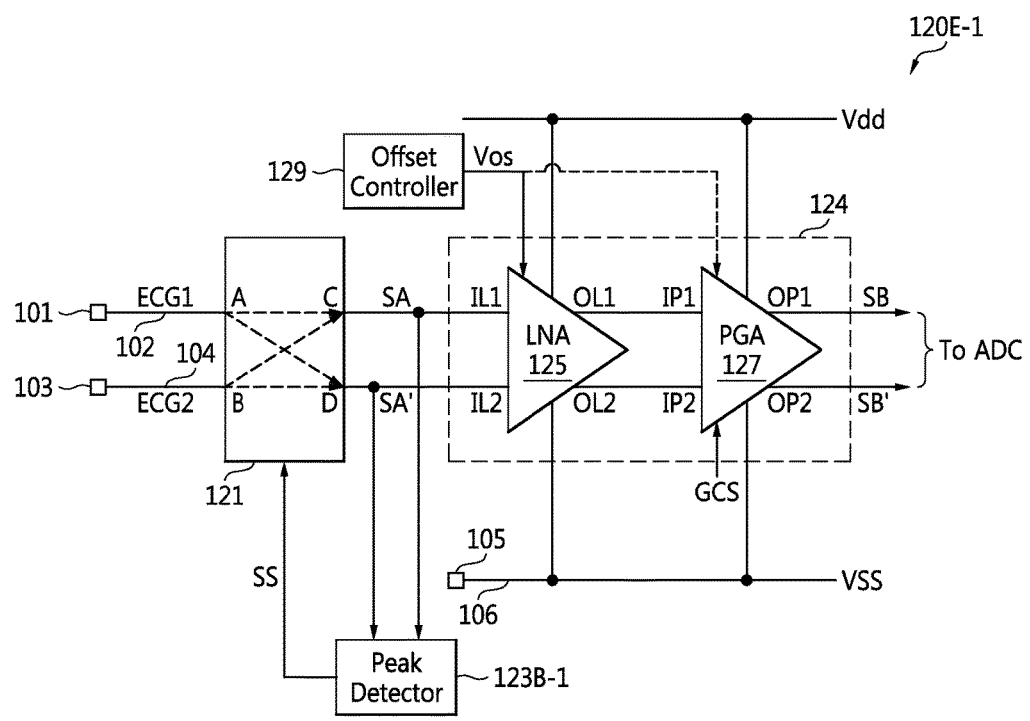
Figure 10B:
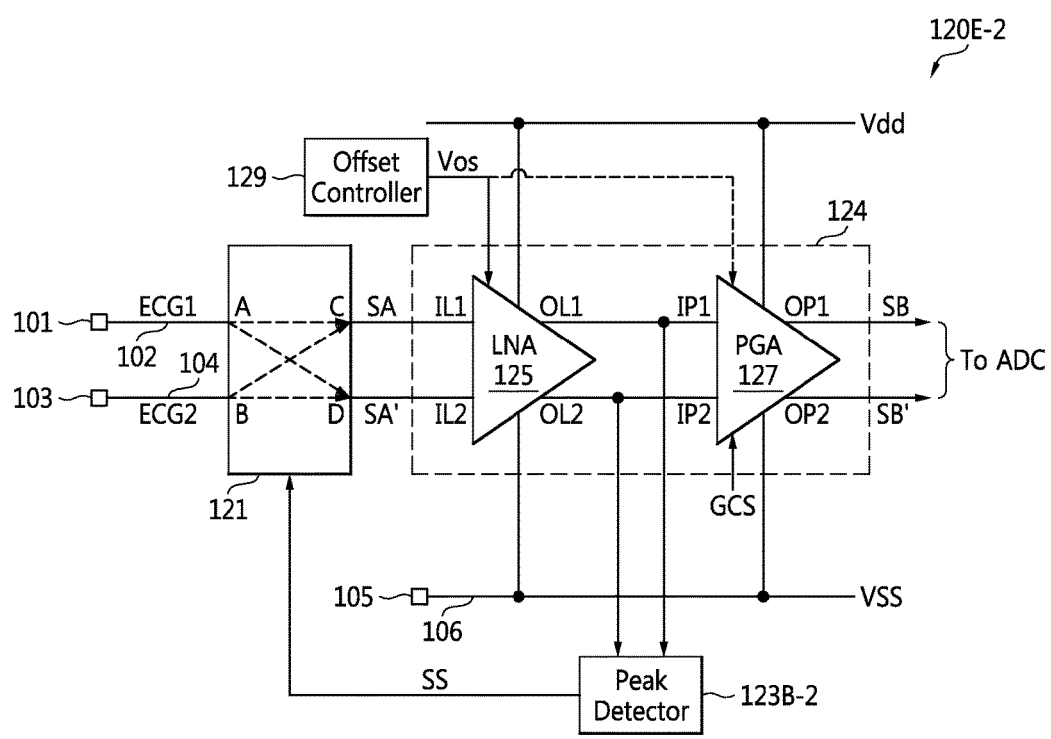
Figure 10C:
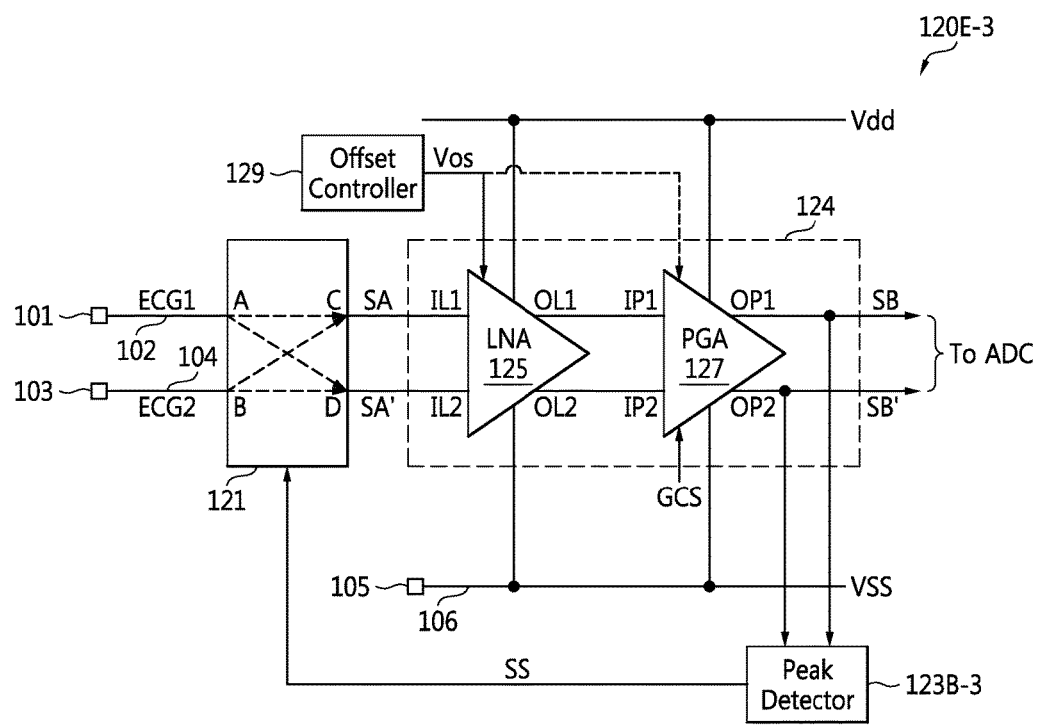
Figure 11:
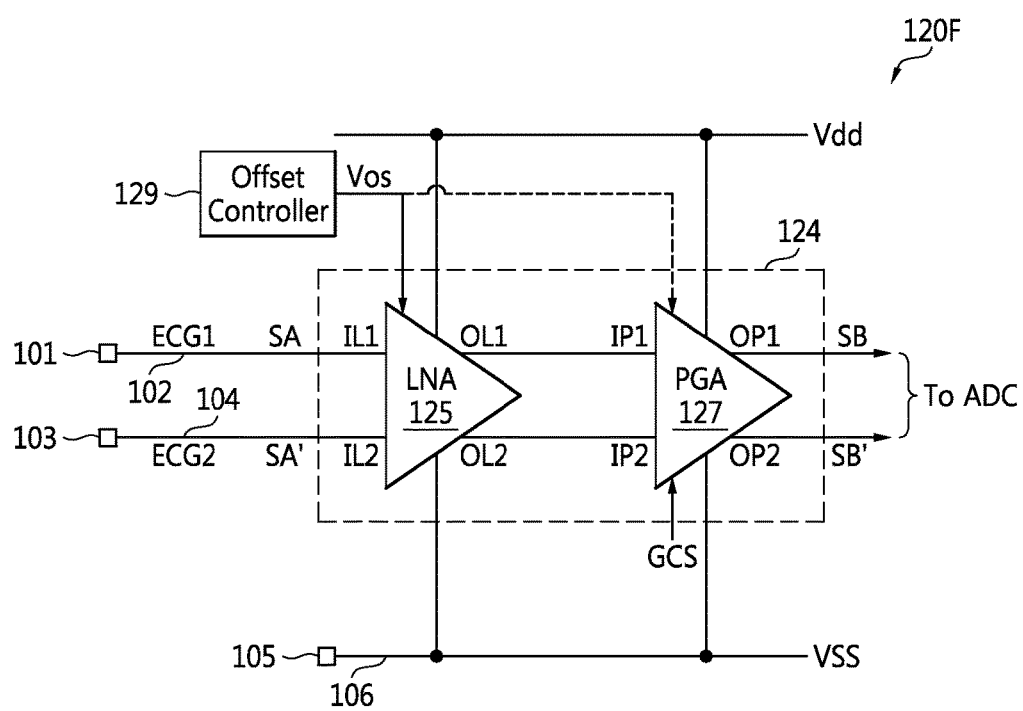

The embodiments of the inventive concept illustrated in FIGS. 9, 10 and 11 (120D, 120E and 120F) are respectively analogous to the embodiments previously described in relation to FIGS. 5, 6 and 7 (120A, 120B and 120C). However, in each one of the embodiments illustrated in FIGS. 9, 10 and 11 (120D, 120E and 120F), the amplifier 124 has been modified to include an offset controller 129 that provides voltage control offsets to one or both of the LNA 125 and PGA 127. Thus, the differential amplifier 124 included in each of these additional embodiments functions as a differential amplifier with an offset characteristics.

Figure 12A:
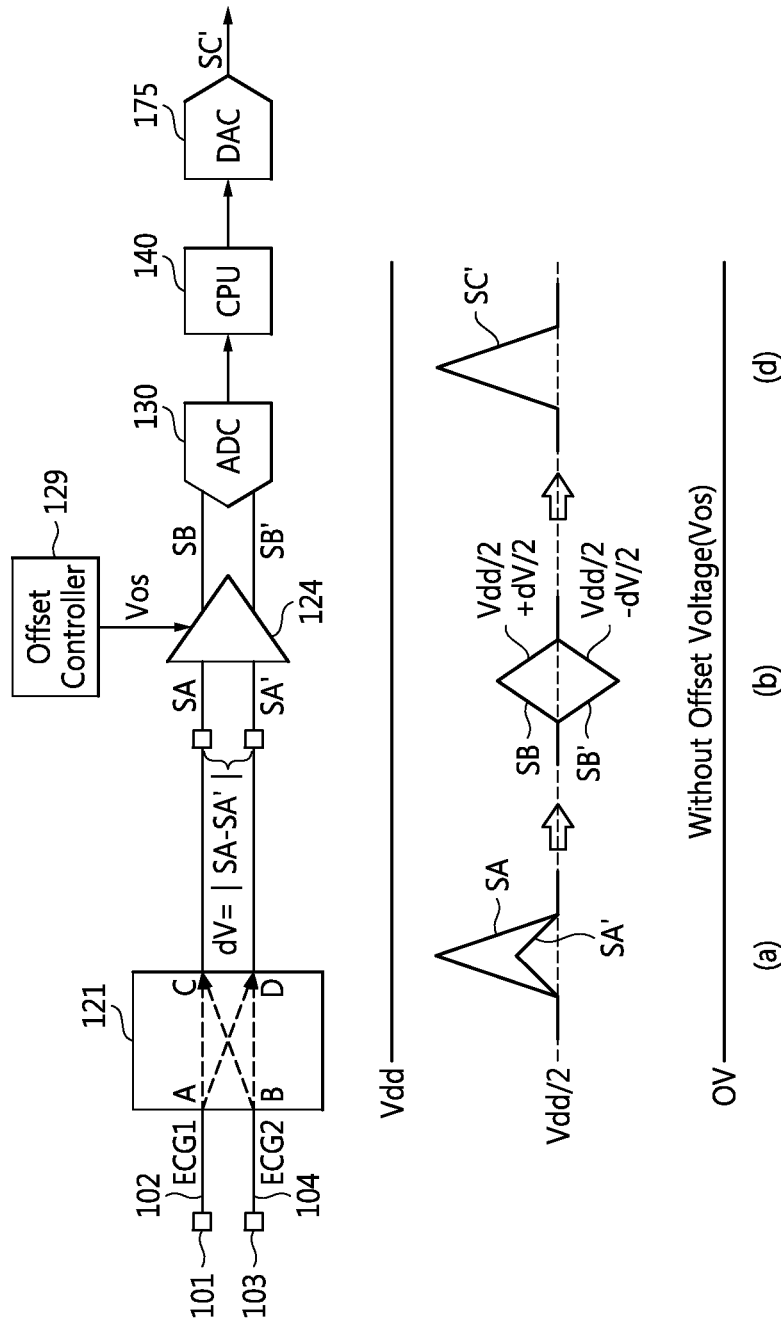

FIG. 12 is a conceptual diagram illustrating a general approach whereby offset voltages are used in conjunction with the amplifier 124 to generate an amplified ECG signal (SC) that is more easily discriminated. Referring to FIG. 12 and holding in mind the previous descriptions of the embodiments illustrated in FIGS. 4, 5, 6 and 7, a digital-to-analog converter (DAC) 175 is added behind the ADC 130. Here, the DAC 175 may be provided as part of the display controller 170 or display 180. That is, the display 180 may include a display driver IC having the DAC 175.

A voltage difference "dV" is equal to the absolute value of a difference between the first ECG signal (SA) and the second ECG signal (SA'), where operating voltages of Vdd and 0V are assumed for the LNA 125 and PGA 127. During the differential amplification with voltage offset of the first and second ECG signals, as shown in FIG. 12, the first ECG signal SA applied to a first input of the LNA 125 and the second ECG signal SA' applied to a second input of the LNA 125 have the relationship shown at (a) of FIG. 12.

Before an offset voltage (Vos) is applied to the differential amplifier 124, and particularly to the LNA 125, the ECG output signals SB and SB' provided by the differential amplifier 124 will be symmetrical around Vdd/2 as shown in (b) of FIG. 12. Thus, when the offset voltage is not applied to the differential amplifier 124, an amplified differential output signal SC' provided to the DAC 175 will be as shown in (d) of FIG. 12. This generated version of the amplified differential ECG signal SC' extends over only about half of the voltage range between Vdd and 0V.

However, when the offset voltage is applied to the differential amplifier 124, and particularly to the LNA 125, the output ECG signals SB and SB' of the differential amplifier 124 will again be symmetrical around Vdd/2, but will be modified by the offset voltage value Vos as shown in (c) of FIG. 12. As a result of this offset voltage modification, the amplified differential ECG signal SC illustrated in (e) of FIG. 12 occupies the full operating voltage range.

Of note, the signal-to-noise ratio for the amplified differential ECG signal is much better when an offset voltage is applied. That is, when an offset voltage is applied to the differential amplifier 124, and particularly to the LNA 125, the difference between the first and second ECG signals is more pronouncedly amplified.

As shown in FIGS. 9, 10 and 11, one or more offset voltages (singularly or collectively, Vos) provided by the offset controller 129 may be applied one or both of the LNA 125 and PGA 127. A first offset voltage applied to the LNA 125 may be the same or different from a second offset voltage applied to the PGA 127.

Figure 13:
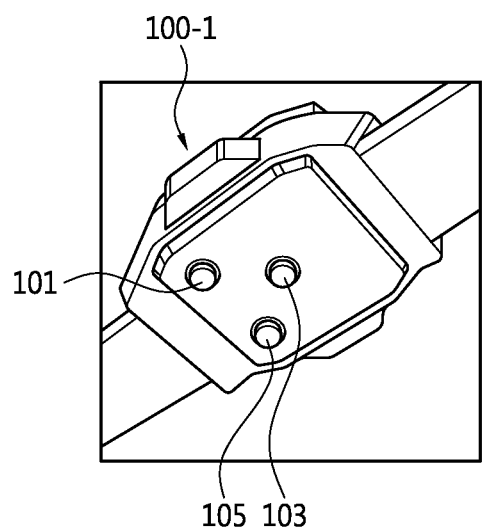
FIGS. 13, 14, 15, 16A and 16B are respective, perspective diagrams variously illustrating in different examples certain wearable appliances capable of capturing an ECG signal according to embodiments of the inventive concept.

FIG. 13 is a perspective diagram illustrating a wearable appliance 100-1 capable of capturing and processing one or more ECG signal(s) according to certain embodiments of the inventive concept. Referring to FIG. 13, the wearable appliance 100-1 again takes the form of a wrist watch, but now includes the first electrode 101, second electrode 103, and ground electrode 105 commonly arranged proximate one another on a bottom surface of the watch 100-1. A processing unit 110 and display 180 similar to those previously described may be included in the wearable appliance 100-1. Optionally, the wearable appliance 100-1 may also include the input device 185 and/or the user-activated location input device (e.g., button) 107 previously described.

Figure 14:
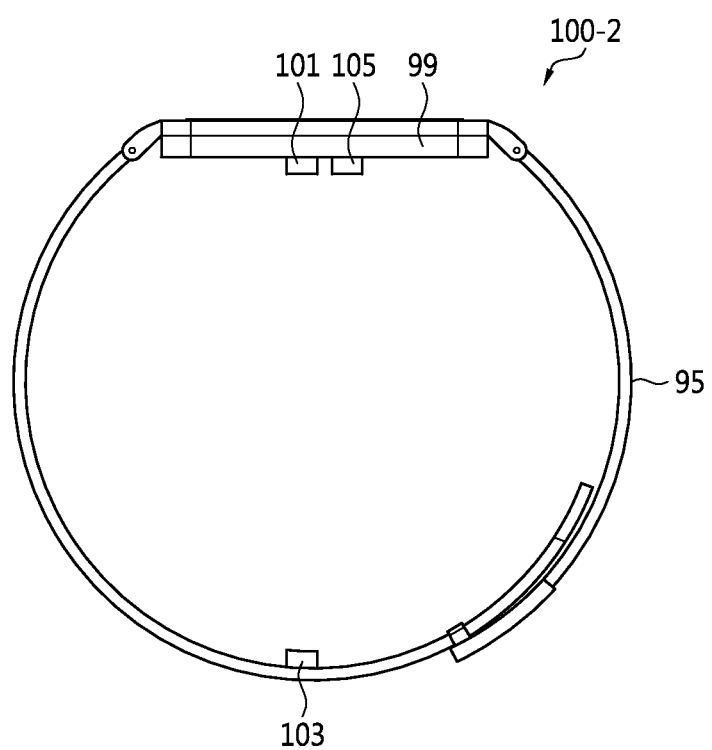

FIG. 14 is a perspective diagram illustrating a wearable appliance 100-2 capable of capturing and processing one or more ECG signal(s) according to certain embodiments of the inventive concept. Referring to FIG. 14, the wearable appliance 100-2 again takes the form of a wrist watch and includes first electrode 101 and ground electrode 105 protruding from a bottom surface of watch body 99 supported on the user's wrist by a watch strap 95. The second electrode 103 is arranged on a portion of the watch strap 95 directly opposite the watch body 99. Here again, the processing unit 110, display 180, user input 185 and/or user-activated location input device 107 previously described may be included in the wearable appliance 100-2.

Figure 15:
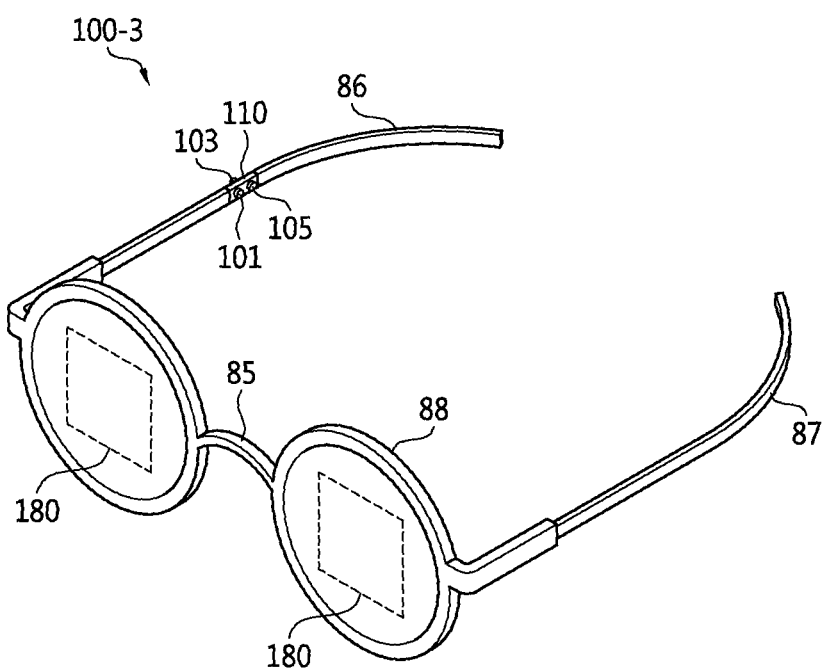

FIG. 15 is a perspective diagram illustrating a wearable appliance 100-3 capable of capturing and processing one or more ECG signal(s) according to certain embodiments of the inventive concept. The eye glasses-wearable appliance 100-3 includes one or more of first, second and ground electrodes 101, 103, and 105, as previously described, processing unit 110, and optionally, one or more displays 180, where the eye glasses 100-3 include left and right lens parts 88 connected by a bridge part 85, a left arm member 87 supporting the eye glasses on a left side of a user's head, and a right arm member 86 supporting the eye glasses on a right side of the user's head.

Although the eye glasses of FIG. 15 are illustrated as having the first electrode 101, second electrode 103 and ground electrode 105 disposed closely proximate one to another on a single arm member, this need not always be the case. For example, the second electrode 103 may be disposed on the opposing left arm member 87 instead of the right arm member 86 having the first electrode 101 and ground electrode 105. Further, one or more displays 180 may be incorporated within one or both of the lens parts 88.

In certain embodiments of the inventive concept, the processing unit 110 and a power source may be provided on a SoC disposed on one or both arm member(s) 87/86 of the eye glasses 100-3 along with one or more ECG sensors 101, 103 and 105. However, one or more of the ECG sensors 101, 130 and 105 may be separately disposed on the eye glasses 100-3 external to the SoC.

Figure 16A:
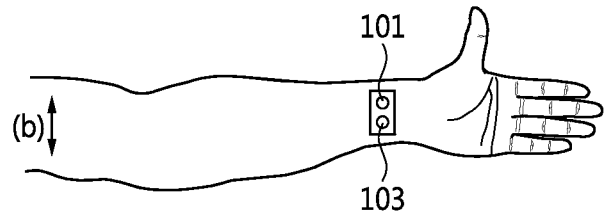
Figure 16B:
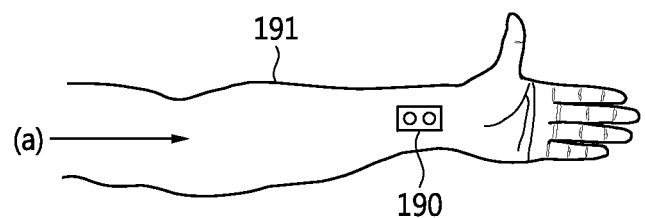

FIG. 16, inclusive of FIGS. 16A and 16B, is a perspective diagram illustrating a wearable appliance 100-4 capable of capturing and processing one or more ECG signal(s) according to certain embodiments of the inventive concept. Here, the wearable appliance 100-4 takes the form of a skin-adhering patch 190 that may be directly applied to a desired location by a user. One or more ECG-sensing electrodes (e.g., first ECG electrode 101 and second ECG electrode 1030 may be incorporated within the patch 190, along with a processing unit 110 consistent with the previously described embodiments.

Of particular note, the arrangement of the sensors in patch 190 of FIG. 16B "along" the direction of the primary veins running through the user's arm 191 (i.e., direction "a") has been found to be more effective in facilitating the capture of an ECG signal than the arrangement of the sensors in patch 190 of FIG. 16A "across" the direction of the primary veins running through the user's arm 191 (i.e., direction "b").

The embodiment of FIG. 16 is drawn to a user's lower arm, but those skilled in the art will understand from the foregoing description that other patch-embodiments consistent with the inventive concept may be configured for use in relation to other user locations such as the upper arm, upper or lower leg, neck, etc.

Figure 17:
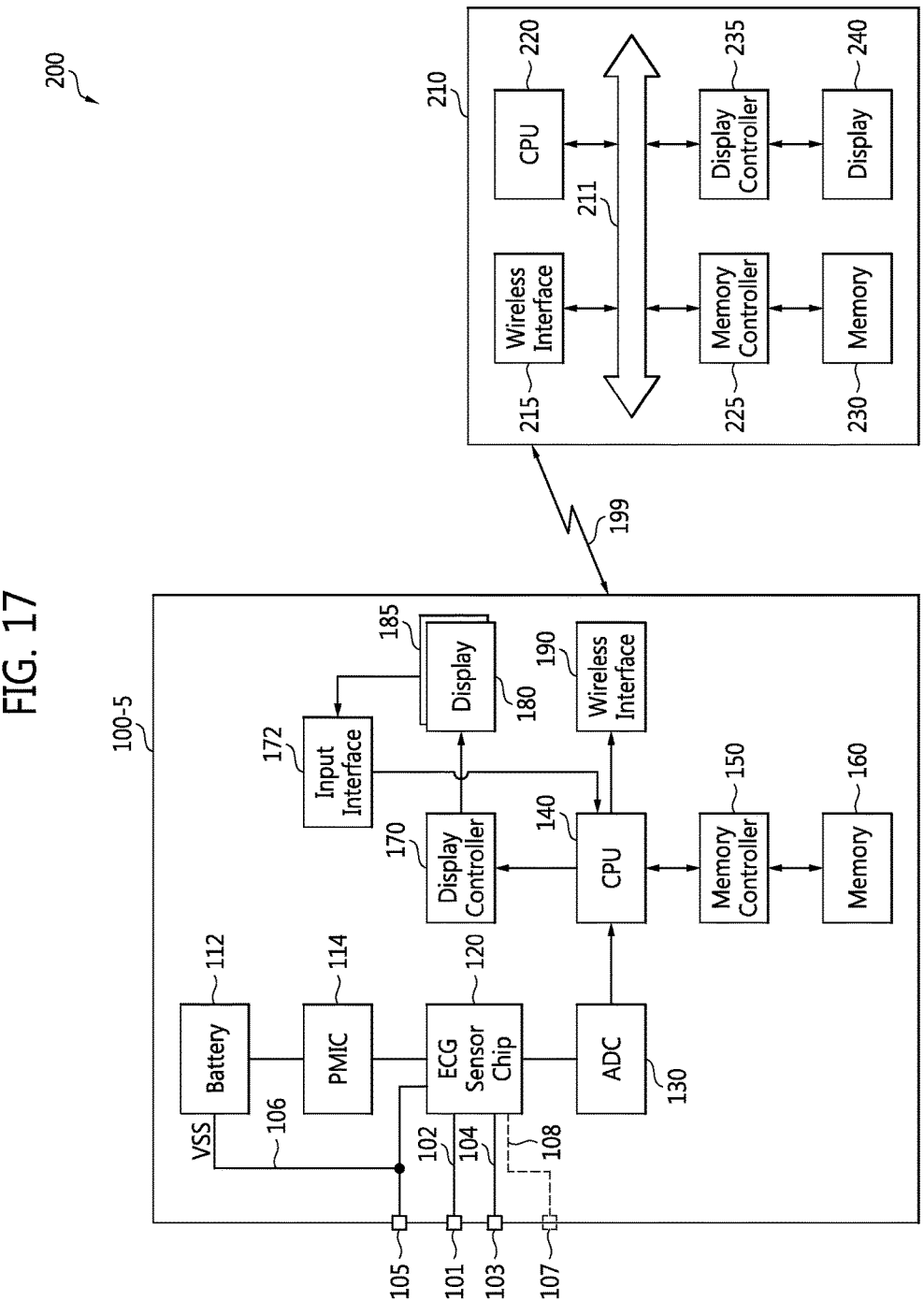
FIG. 17 is a block diagram of a data processing system including a wearable appliance including an ECG sensor chip according to embodiments of the inventive concept.

FIG. 17 is a block diagram of a data processing system 200 including a wearable appliance 100-5 including the ECG sensor chip 120 FIG. 4 according to embodiments of the inventive concept. Referring to FIG. 17, the data processing system 200 includes the wearable appliance 100-5 and a computing device 210 configured to communicate with the wearable appliance via a wireless and/or a hard-wired connection 199.

The wearable appliance 100-5 may be configured like the wearable appliance previously described in relation to FIG. 4, except for the additional provision of a wireless interface 190. The wireless interface 190 may be used to communicate data processed by the CPU 140 to the computing device 210 using the wireless connection 199. The data may include data related with an ECG signal (or ECG waveform), data related with a heart rate, and/or data related with arrhythmia. The wireless interface 190 may support Bluetooth, Bluetooth low energy (BLE), near field communication (NFC), radio-frequency identification (RFID), or WiFi.

The computing device 210 illustrated in FIG. 17 comprises; a wireless interface 215, a CPU 220, a memory controller 225, a memory 230, a display controller 235, and a display 240. The computing device 210 may be implemented as a mobile computing device or a server. The server may be used to provide a telemedicine service, for example.

The wireless interface 215, the CPU 220, the memory controller 225, the memory 230, the display controller 235, and the display 240 may communicate with one another through a bus structure 211. The wireless interface 215 may communicate with the wireless interface 190. The wireless interface 215 may support Bluetooth, BLE, NFC, RFID, or WiFi.

The CPU 220 may control the memory controller 225 and the display controller 235 through the bus structure 211.

The memory controller 225 may write data (e.g., data about an ECG) to the memory 230 or may read data (e.g., data about an ECG) from the memory 230 according to the control of the CPU 220. The memory 230 may be implemented using volatile and/or non-volatile memory.

The display controller 235 may transmit data from the CPU 220 or the memory controller 225 to the display 240 through interface according to the control of the CPU 220. The data may include data related with an ECG signal (or ECG waveform), data related with a heart rate, and/or data related with arrhythmia.

Figure 18:
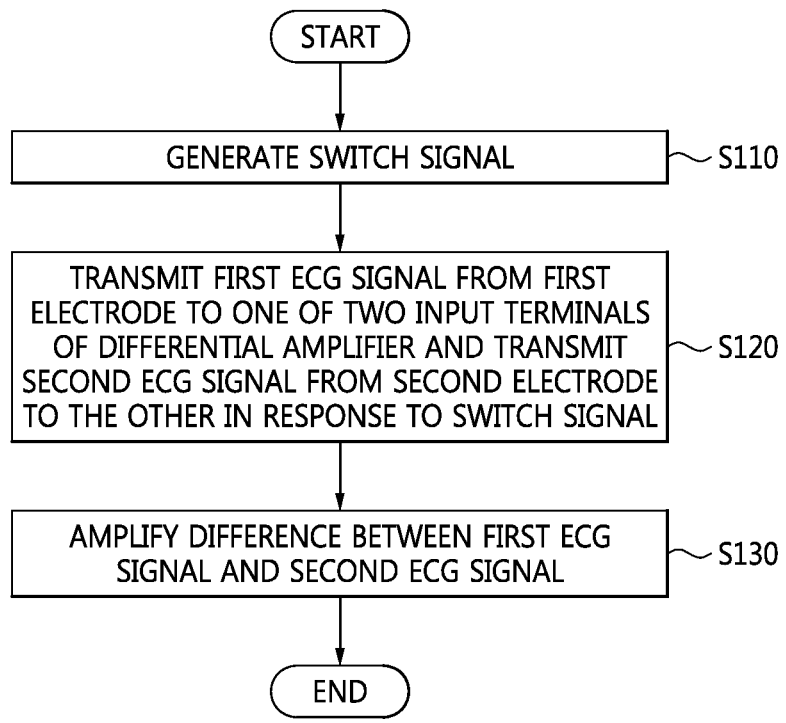
FIG. 18 is a flowchart generally summarizing a method of operating an ECG sensor chip according to embodiments of the inventive concept.

FIG. 18 is a flowchart summarizing a method of using an ECG sensor chip in a wearable appliance according to certain embodiments of the inventive concept. Referring to FIGS. 4, 5 and 6, as well as FIGS. 13, 14, 15, 16 and 17, the switch signal generator 123A or the peak detector 123B may be used to generate the switch signal (SS) and then communicate the switch signal to the switch circuit 121 (S110). As described above, in response to the switch signal having the first level, the switch circuit 121 will pass the first ECG signal ECG1 received via the first input terminal A to the first output terminal C and the second ECG signal ECG2 received via the second input terminal B to the second output terminal D. Alternately, in response to the switch signal having the second level, the switch circuit 121 will pass the first ECG signal ECG1 received via the first input terminal A to the second output terminal D and the second ECG signal ECG2 received via the second input terminal B to the first output terminal C (S120).

The differential amplifier 124 then amplifies the difference between the first ECG signal (SA) apparent at the first input terminal IL1 and the second ECG signal (SA') apparent at the second input terminal IL2, and output the amplified ECG output signals (SB and SB') to the ADC 130 (S130).

As described above with reference to FIGS. 9 and 10, when the offset controller 129 applies the offset voltage Vos to the differential amplifier 124, the differential amplifier 124 may output the amplified signals SB and SB' reflecting the offset voltage Vos to the ADC 130, as described with reference to FIG. 12 and with respect to operation S130.

Figure 19:
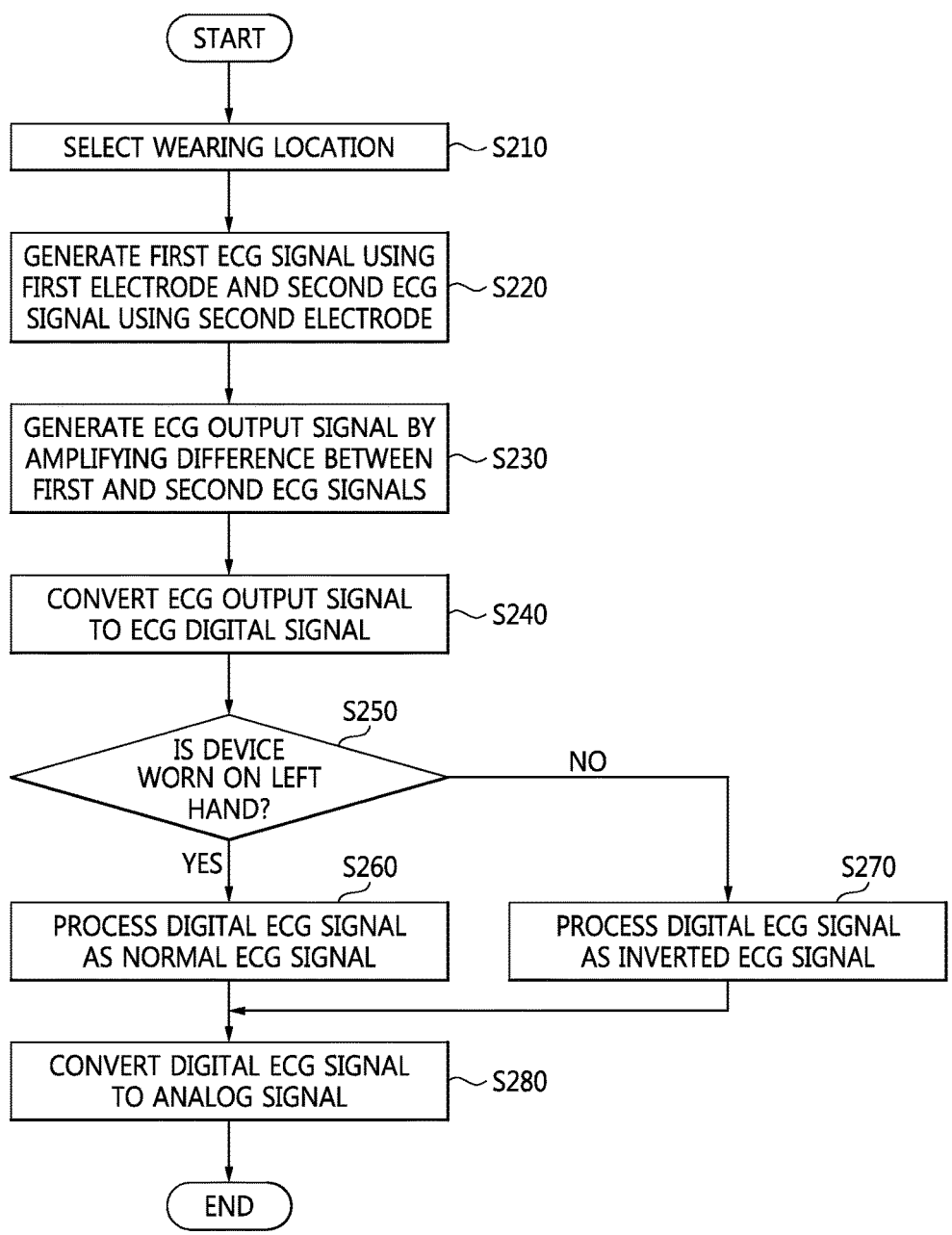
FIG. 19 is a flowchart summarizing a method of selectively operating a wearable appliance according to embodiments of the inventive concept.

FIG. 19 is a flowchart summarizing a method of using a wearable appliance according to certain embodiments of the inventive concept. Referring to FIGS. 4, 7, 11, 13, 14, 15, 16 and 18, a user of the wearable appliance (e.g., 100, 100-1, 100-2, 100-3, 100-4 or 100-5) may select an icon (182 or 184) from the GUI 181 displayed on the display 180 using the input device 185 (S210) before beginning the process of ECG signal capture.

Here, it is assumed that the first electrode 101 and ground electrode 105 are placed in contact with one of the left hand or right hand, while the second electrode 103 is contacted by the other one of the left hand or right hand. As a result, the first electrode 101 generates the first ECG signal and the second electrode 103 generates the second ECG signal ECG2 (S220).

The differential amplifier 124 is then used to amplify a difference between the first ECG signal and second ECG signal, generate amplified ECG output signals (SB and SB'), and communicate the amplified ECG output signals to the ADC 130 (S230). The ADC 130 then converts the amplified ECG output signals SB and SB' into corresponding digital ECG signals (S240).

When the user selected an icon (e.g. 182) during operation S210, corresponding location information was communicated to the CPU 140 via input device 185 and user interface 172. Thus, under the foregoing assumptions, when the wearable appliance is worn on the left wrist and a finger of the right hand makes contact with the second electrode 103, an ECG signal having the waveform of FIG. 3A is generated. Accordingly, the CPU 140 processes the resulting digital ECG signals provided by the ADC 130 based on the location information by processing the digital ECG signal as a normal (or non-inverted) ECG signal (S260).

However, assuming that the user selected the icon 184 in operation S210, different location information is communicated to the CPU 140 via the input device 185 and user interface 172. Thus, when the wearable appliance is worn on the right wrist and a finger of the left hand makes contact with the second electrode 103, the resulting ECG signal will have the waveform of FIG. 3B. Accordingly, the CPU 140 will process the corresponding digital ECG signal provided by from the ADC 130 based on the location information and process the digital ECG signal as an inverted ECG signal (S270).

Thereafter, the display controller 170 or the DAC 175 of the display 180 may be used to converts certain digital control signal/data provided by the CPU 140 into one or more analog signal(s) (S280).

Figure 20:
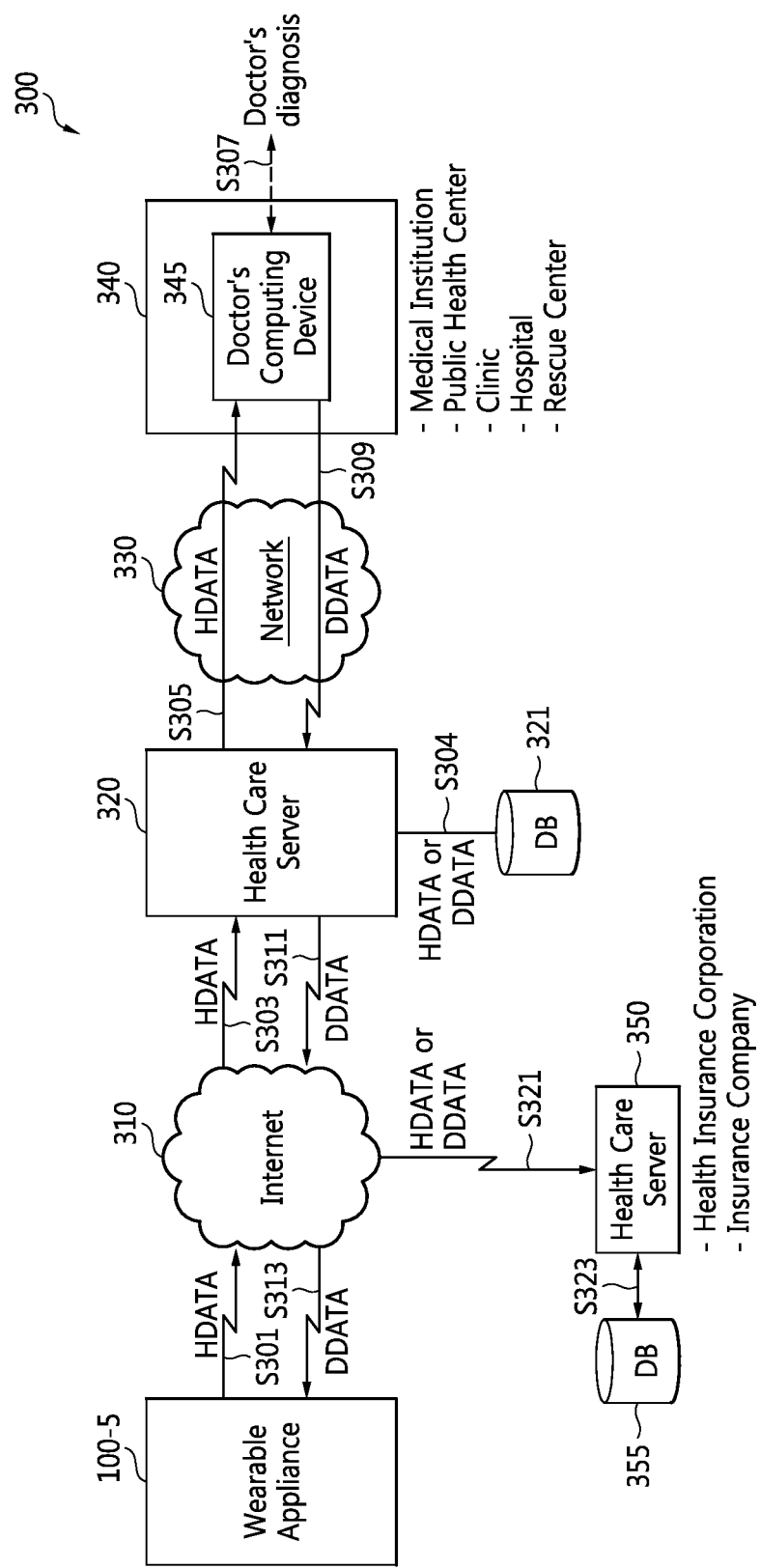
FIGS. 20 and 21 are respective block diagrams of data processing systems including a wearable appliance including the ECG sensor chip according to certain embodiments of the inventive concept.

FIG. 20 is a block diagram of a data processing system 300 including a wearable appliance 100-5 including an ECG sensor chip like the one described in relation to FIG. 4 according to certain embodiments of the inventive concept. The data processing system 300 may be used to provide one or more tele-medicine service(s) adapted to monitor, record, characterize and/or protect the health of a user wearing the wearable appliance 100-5.

Thus, referring to FIG. 20, the data processing system 300 includes the wearable appliance 100-5 and a first health care server 320 configured to communicate data derived or monitored by the wearable appliance via a wireless network (e.g., the internet 310, or similar distributed, wireless communication system). In certain embodiments of the inventive concept, the data processing system 300 may further include a second health care server 350 similarly configured to communicate with the wearable appliance 100-5 and/or the first health care server 320. Here, for example, it is assumed that an insurance entity manages the second health care server 350 and its constituent database 355.

When the user of the wearable appliance 100-5 causes the execute of an application installed in the wearable appliance 100-5, a wireless interface of the wearable appliance 100-5 will communicate health-related data (HDATA) to the health care server 320 via the internet 310 (S301). It is assumed that the application is capable of storing a uniform resource locator (URL) associated with the first health care server 320 and/or the second health care server 350. Thus, the application may be used to communicate health data (HDATA) to the first health care server 320 and/or the second health care server 350 using the URL.

The wireless network 310 may be used to communicate the heath data (HDATA) to the first health care server 320 (S303) and/or the second health care server 320 (S321). In this regard, the health data may include data associated with or derived from one or more ECG signal(s), including data related indicating the user's heart rate.

The first health care server 320 receives the health data (S303), may store it, as necessary, in a constituent database 321 (S304), and communicate the health data—or data derived from the heath data—to a doctor's computing device 345 via the network 330 (S305). In this context, the doctor's computing device 345 may be a personal computer (PC) or a tablet PC. Assuming that the doctor works at a medical institution (e.g., a private medical practice, public health care center, clinic, hospital, or rescue center 340), his/her computing device may be administered or integrated with a larger patient data system in order to monitor received health data, and diagnose the user's medical state. In response to the health data, the doctor and/or his/her representative(s) may then input diagnostic data (DDATA) (e.g., information related to a doctor's counsel or diagnosis) to the doctor's computing device 345 (S307). The doctor's computing device 345 may then communicate the diagnostic data to the first health care server 320 via the network 330 (S309). The first health care server 320 receives the diagnostic data, stores it in the database 321 (S304), and communicates it to the wearable appliance 100-5 and/or the second health care server 350 via the wireless network 310 (S311, S313 and/or S321). In response to the diagnostic data, the wearable appliance 100-5 may display the certain data via its display 185 under the control of the application executed by the CPU 140, and in certain embodiments of the inventive concept, the second health care server 350 may store the diagnostic data in the database 355 (S323).

In this manner, the user of the wearable appliance 100-5 may receive diagnostic data from a health care professional is something approximating real time communications, depending on the medical professional's ability to receive and respond to the health data communicated by the wearable appliance 100-5.

Figure 21:
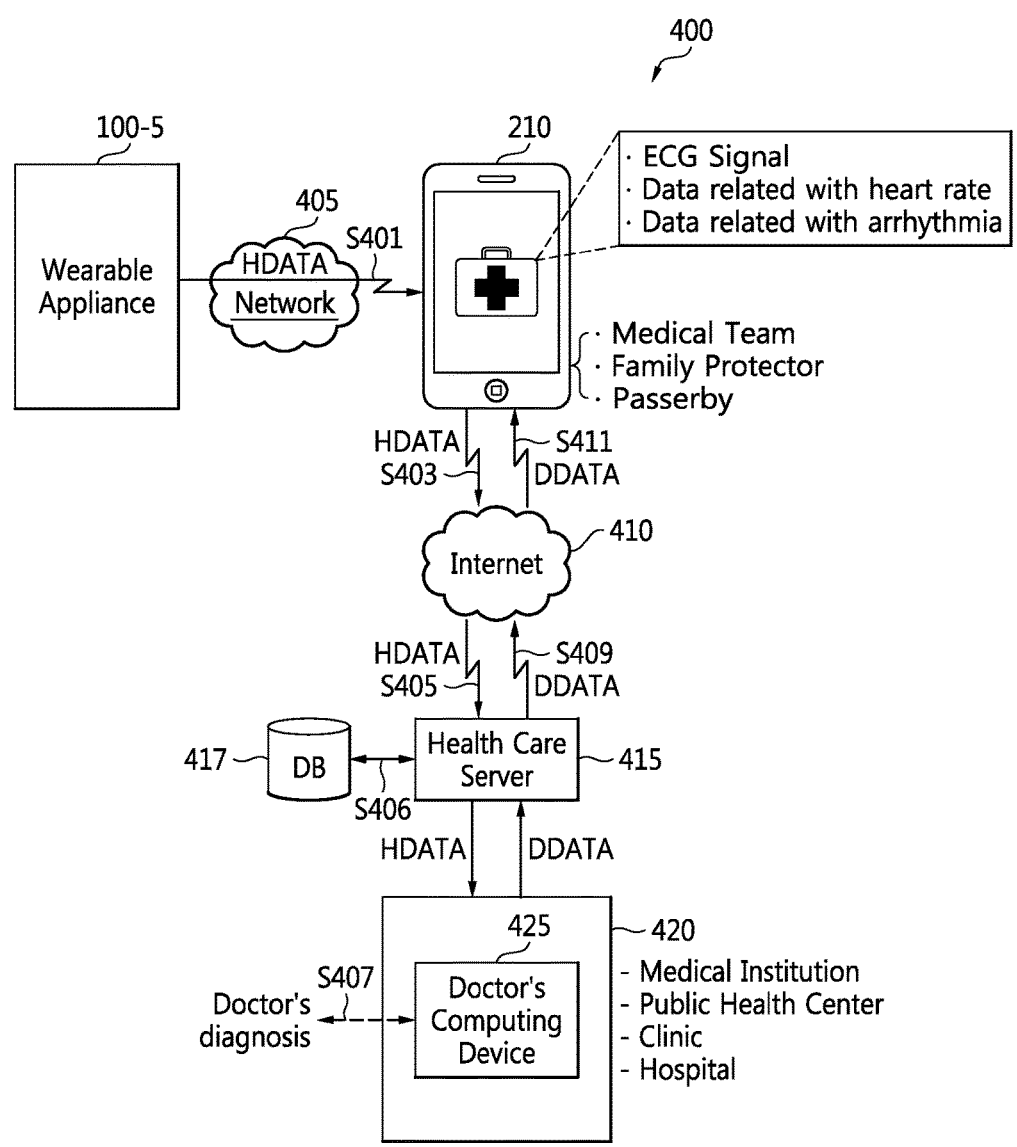

FIG. 21 is a block diagram of a data processing system 400 including a wearable appliance 100-5 including the ECG sensor chip like the one described in relation to FIG. 4 according to certain embodiments of the inventive concept. Like the data processing system 300 of FIG. 20, the data processing system 400 of FIG. 21 may be used to provide one or more tele-medicine services.

Referring to FIG. 21, the data processing system 400 includes the wearable appliance 100-5 and a computing device 210 configured to communicate with the wearable appliance 100-5 via a wireless network (e.g., an internet 405). According to some embodiments, the data processing system 400 may further include health care server 415 configured to communicate with the computing device 210 via a wireless network (e.g., an internet 410.

When a user of the wearable appliance 100-5 causes execute of an application installed in the wearable appliance 100-5, a wireless interface of the wearable appliance 100-5 will communicate health data (HDATA) to the computing device 210 via the wireless network 405 (S401). The health data may include one or more ECG signal(s) indicating the user's heart rate.

In certain embodiments of the inventive concept, the computing device 210 may receive the health data from the wearable appliance 100-5 via a near field communication (NFC) scanning method or tagging method. Here, it is assumed that an application capable of receiving the health data from the wearable appliance 100-5 is installed on the computing device 210. For example, the wearable appliance 100-5 may operate as a NFC tag and the computing device 210 may operate as NFC reader. As described above, the application installed in the computing device 210 may store a URL associated with a health care server 415 configured to communicate with the computing device 210 and a doctor's computing device 425.

When the doctor's computing device 210 receives the health data from the wearable appliance 100-5, the computing device 210 may generate an indication and/or display the health data or data derived therefrom. If the doctor's intervention is warranted, the computing device 210 may be used to communicate diagnostic data (DDATA) and the health data to the health care server 415 via an internet 410 under the control of an application controlled by the doctor or his/her medical team. Thus, the application may communicate the health data to the health care server 415 using the URL of the health care server 415.

In this manner, the health care server 415 may receive the health data (S405), stores it in a constituent database 417 (S406), and communicate the health data to a doctor's computing device 425 via a network. Here again, the network may be a wired communication network and/or a wireless communication network, and doctor's computing device 425 may be a personal computer (PC) or a tablet PC.

Where the doctor works in a medical institution, public health care center, clinic, hospital, or rescue center 420, the computing device 425 may be functionally integrated with patent services systems used to monitor health data and diagnose a user's medical state. The doctor may input diagnostic data in response to the health data to the doctor's computing device 425 (S407). The doctor's computing device 425 may then communicate the diagnostic data to the health care server 415 via the network.

The health care server 415 then receives the diagnostic data, stores it in the database 417, and communicates it to the computing device 210 via the wireless internet 410 (S409 and S411). The computing device 210 may display the data DDATA via a display 185 under the control of the application program executed by the CPU 140.

In some certain embodiments, if the user has an emergency, the medical team, the family protector, or the passerby may perform emergency treatment for the user in response to the diagnostic data displayed by the computing device 210. For example, if necessary, the medical team, family protector, or passerby may engage in a video call with the doctor using the computing device 210. Accordingly, the medical team, family protector, or passerby may administer appropriate emergency treatment to the user under the guidance of the doctor. Further, the medical team, family protector, or passerby may provide real time feedback in response to the doctor's monitoring and/or diagnosis.

According to the foregoing embodiments of the inventive concept, an ECG sensor chip may or may not invert a captured ECG signal according to a switch signal. In addition, the ECG sensor chip using an amplifier configured with an offset controller may be used to reduce noise and improve signal differentiation. According to embodiments of the inventive concept, a wearable appliance will appropriately process one or more ECG signals in response to the location at which the wearable appliance is worn by a user.

The foregoing embodiments are illustrative in nature. The scope of the inventive concept is defined by the following claims and their equivalents.

What is claimed is:

1. An electrocardiogram (ECG) sensor chip configured for use in a wearable appliance and comprising:
   a switch controlled by a switching signal and including a
      first switch input that receives a first ECG signal, a
      second switch input that receives a second ECG signal,
      a first switch output, and a second switch output;

an amplifier including a first amplifier input that receives one of the first ECG signal and the second ECG signal from the first switch output and a second amplifier input that receives the other one of the first ECG signal and the second ECG signal from the second switch output, and amplifies a difference between the first ECG signal and second ECG signal; and a location indicator that generates the switching signal in one of a first state and a second state based on a distance between a single location of the wearable appliance at which the first ECG signal is captured on a user's body and a location of a heart of the user as determined by comparing a relative strength of the first ECG signal from between the first switch output and the first amplifier input and a relative strength of the second ECG signal from between the second switch output and the second amplifier input, wherein, in response to the first state of the switching signal, the switch passes the first ECG signal from the first switch input to the first switch output and passes the second ECG signal from the second switch input to the second switch output, and in response to the second state of the switching signal, the switch passes the first ECG signal from the first switch input to the second switch output and passes the second ECG signal from the second switch input to the first switch output.

2. The ECG sensor chip of claim 1,
wherein the location indicator comprises a switch signal generator that generates the switching signal in one of the first state and the second state in response to an indication signal,
wherein the switching signal has the first state when the distance between the location at which the first ECG signal is captured on the user's body and the location of the user's heart corresponds to an amplified signal in a first range, and
wherein the switching signal has the second state when the distance between the location at which the first ECG signal is captured on the user's body and the location of the user's heart corresponds to the amplified signal in a second range.

3. The ECG sensor chip of claim 2,
wherein the indication signal is generated in response to user activation/deactivation of a dedicated user-activated location input element on the wearable appliance that identifies the location of the wearable appliance.

4. The ECG sensor chip of claim 1,
wherein the location indicator comprises a peak detector that receives a first peak detection signal derived from the first ECG signal and a second peak detection signal derived from the second ECG signal and generates the switching signal based on a difference between the first peak detection signal and the second peak detection signal.

5. The ECG sensor chip of claim 4, wherein the amplifier comprises:
a front-end low noise amplifier (LNA) that receives the first ECG signal and second ECG signal from the switch, and generates an intermediate amplified first ECG signal and an intermediate amplified second ECG signal; and
a back-end programmable gain amplifier (PGA) that receives the intermediate amplified first ECG signal and the intermediate amplified second ECG signal from the LNA, and generates an amplified first ECG signal and an amplified second ECG signal.

6. The ECG sensor chip of claim 5, further comprising:
an offset controller that provides at least voltage control offset to at least one of the LNA and PGA.

7. The ECG sensor chip of claim 1,
wherein the switching signal has the first state when the wearable appliance is determined to be worn on a left wrist of the user, and the switching signal has the second state when the wearable appliance is determined to be worn on a right wrist of the user.

8. A wearable appliance adapted to be worn at a location on a user and comprising:
a first electrocardiogram (ECG) electrode;
a second ECG electrode;
an ECG sensor chip that receives a first ECG signal from the first ECG electrode and a second ECG signal from the second ECG electrode, the ECG sensor chip comprising;
a switch controlled by a switching signal and including a first switch input that receives the first ECG signal, a second switch input that receives the second ECG signal, a first switch output, and a second switch output;
an amplifier including a first amplifier input that receives one of the first ECG signal and the second ECG signal from the first switch output and a second amplifier input that receives the other one of the first ECG signal and the second ECG signal from the second switch output, and generates an amplified difference signal between the first ECG signal and the second ECG signal; and
a location indicator that generates the switching signal in one of a first state and a second state based on a distance between a single location of the wearable appliance at which the first ECG signal is captured on a user's body and a location of a heart of the user as determined by comparing a relative strength of the first ECG signal from between the first switch output and the first amplifier input and a relative strength of the second ECG signal from between the second switch output and the second amplifier input,
wherein, in response to the first state of the switching signal, the switch passes the first ECG signal from the first switch input to the first switch output and passes the second ECG signal from the second switch input to the second switch output, and in response to the second state of the switching signal, the switch passes the first ECG signal from the first switch input to the second switch output and passes the second ECG signal from the second switch input to the first switch output.

9. The wearable appliance of claim 8,
wherein the first ECG electrode is disposed on a first surface of the wearable appliance, and the second ECG electrode is disposed on a second surface of the wearable appliance different from the first surface.

10. The wearable appliance of claim 9, further comprising:
a ground electrode disposed on a third surface of the wearable appliance and in contact with the user at the location when the wearable appliance is worn by the user.

11. The wearable appliance of claim 10,
wherein the first surface and third surface are a same surface of the wearable appliance, such that the ground electrode and first ECG electrode are proximately disposed on the same surface of the wearable appliance and in contact with the user at the location when the wearable appliance is worn by the user.

12. The wearable appliance of claim 10,
wherein the wearable appliance is a watch comprising a watch body and a watch strap adapted to attach the watch body to a wrist of the user,
the first surface and third surface are a bottom surface of the watch body and in contact with the wrist of the user when the watch is worn by the user, and
the second surface is a portion of the watch strap.

13. The wearable appliance of claim 8,
wherein the first ECG electrode, second ECG electrode and a ground electrode are commonly disposed on a surface of the wearable appliance and in contact with the user at the location when the wearable appliance is worn by the user.

14. The wearable appliance of claim 8,
wherein the wearable appliance is a watch, and the location is a wrist of the user.

15. The wearable appliance of claim 8,
wherein the wearable appliance is a patch configured to adhere to the skin of the user.

16. The wearable appliance of claim 8, wherein the wearable appliance is eye glasses, comprising:
left and right lens parts connected by a bridge part;
a left arm member adapted to support the eye glasses on a left side of a user's head; and
a right arm member adapted to support the eye glasses on a right side of the user's head,
wherein at least one of the first ECG electrode and second ECG electrode is disposed on one of the left arm member and right arm member and in contact with the user's head when the glasses are worn by the user.

17. The ECG sensor chip of claim 8,
wherein the location indicator comprises a switch signal generator that generates the switching signal in one of the first state and the second state in response to an indication signal,
wherein the switching signal has the first state when the distance between the location at which the first ECG signal is captured on the user's body and the location of the user's heart corresponds to an amplified signal in a first range, and
wherein the switching signal has the second state when the distance between the location at which the first ECG signal is captured on the user's body and the location of the user's heart corresponds to the amplified signal in a second range.

18. The ECG sensor chip of claim 8,
wherein the switching signal has the first state when the wearable appliance is determined to be worn on a left wrist of the user, and the switching signal has the second state when the wearable appliance is determined to be worn on a right wrist of the user.

19. A system on a chip (SoC) comprising: an electrocardiogram (ECG) sensor chip that includes:
a switch controlled by a switching signal and including a first switch input that receives a first ECG signal from a first ECG sensor, a second switch input that receives a second ECG signal from a second ECG sensor, a first switch output, and a second switch output;
an amplifier including a first amplifier input that receives one of the first ECG signal and the second ECG signal from the first switch output, and a second amplifier input that receives the other one of the first ECG signal and the second ECG signal from the second switch output and generates an amplified difference signal between the first ECG signal and the second ECG signal; and
a location indicator that generates the switching signal having one of a first state and a second state based on a distance between a single location of the system on a chip at which the first ECG signal is captured on a user's body and a location of a heart of the user as determined by comparing a relative strength of the first ECG signal from between the first switch output and the first amplifier input and a relative strength of the second ECG signal from between the second switch output and the second amplifier input,
wherein, in response to the switching signal having the first state, the switch passes the first ECG signal from the first switch input to the first switch output and passes the second ECG signal from the second switch input to the second switch output, and in response to the switching signal having the second state, the switch passes the first ECG signal from the first switch input to the second switch output and passes the second ECG signal from the second switch input to the first switch out; and
an analog-to-digital converter (ADC) that receives the amplified difference signal and generates corresponding ECG digital signals; and
a Central Processing Unit (CPU) that receives the ECG digital signals and generates display information that controls generation of a visual image on a display.

20. The SoC of claim 19,
wherein the location indicator generates the switching signal in the first state when the first ECG sensor is in contact with a left wrist of the user and the second ECG sensor is in contact with a right hand of the user, and generates the switching signal in the second state when the first ECG sensor is in contact with a right wrist of the user and the second ECG sensor is in contact with a left hand of the user.

21. The SoC of claim 19, further comprising:
a power management circuit that derives at least one power signal from battery power and provides the at least one power signal to the ECG sensor chip, ADC, and CPU; and
a display controller that receives the display information and drives the display to generate the visual image.

22. The SoC of claim 19, further comprising:
a first substrate mounting the ECG sensor chip, ADC and CPU.

23. The SoC of claim 22, further comprising:
a second substrate stacked on the first substrate and mounting a memory that exchanges data with the CPU, and a memory controller that controls in conjunction with the CPU operation of the memory.

24. The ECG sensor chip of claim 19,
wherein the location indicator comprises a switch signal generator that generates the switching signal in one of the first state and the second state in response to an indication signal,
wherein the switching signal has the first state when the distance between the location at which the first ECG signal is captured on the user's body and the location of the user's heart corresponds to an amplified signal in a first range, and
wherein the switching signal has the second state when the distance between the location at which the first ECG signal is captured on the user's body and the location of the user's heart corresponds to the amplified signal in a second range.

25. The ECG sensor chip of claim 19,
wherein the switching signal has the first state when the wearable appliance is worn on a left wrist of the user, and the switching signal has the second state when the wearable appliance is worn on a right wrist of the user.

* * * * *